United States Patent
Sohn et al.

(10) Patent No.: US 12,263,274 B2
(45) Date of Patent: Apr. 1, 2025

(54) MEDICAL IMPLANTS CONTAINING SURFACE MODIFIED WITH GOLD NANOPARTICLES

(71) Applicant: SELJIN CO.LTD., Seongnam-si (KR)

(72) Inventors: Seil Sohn, Seoul (KR); Wan Kyu Ko, Suwon-si (KR); Seong Jun Kim, Goyang-si (KR)

(73) Assignee: SELJIN CO.LTD., Seongnam-si (KR)

( * ) Notice: Subject to any disclaimer, the term of this patent is extended or adjusted under 35 U.S.C. 154(b) by 1031 days.

(21) Appl. No.: 17/092,304

(22) Filed: Nov. 8, 2020

(65) Prior Publication Data

US 2021/0154365 A1 May 27, 2021

Related U.S. Application Data

(63) Continuation-in-part of application No. PCT/KR2019/005501, filed on May 8, 2019.

(51) Int. Cl.
*A61L 27/28* (2006.01)
*A61L 27/04* (2006.01)
*A61L 27/06* (2006.01)
*B82Y 5/00* (2011.01)
*B82Y 30/00* (2011.01)

(52) U.S. Cl.
CPC ............. *A61L 27/28* (2013.01); *A61L 27/047* (2013.01); *A61L 27/06* (2013.01); *A61L 2400/12* (2013.01); *A61L 2400/18* (2013.01); *A61L 2420/02* (2013.01); *A61L 2420/08* (2013.01); *B82Y 5/00* (2013.01); *B82Y 30/00* (2013.01)

(58) Field of Classification Search
CPC ........ A61L 27/047; A61L 27/28; A61L 27/06; A61L 2420/02; A61L 2400/18; A61L 2420/08; A61L 2400/12; B82Y 30/00; B82Y 5/00
See application file for complete search history.

(56) References Cited

U.S. PATENT DOCUMENTS

| 6,753,568 B1* | 6/2004 | Nakazato ............. H01L 29/772 |
| | | 257/314 |
| 6,761,708 B1* | 7/2004 | Chiu ................. A61M 25/0108 |
| | | 604/103.1 |
| 2001/0037144 A1 | 11/2001 | Kim et al. |
| 2010/0255447 A1 | 10/2010 | Biris et al. |

FOREIGN PATENT DOCUMENTS

| KR | 10-2010-0099857 A | 9/2010 |
| KR | 10-2010-0106847 A | 10/2010 |
| KR | 10-2014-0021245 A | 2/2014 |
| KR | 10-2016-0007176 A | 1/2016 |
| KR | 20160007176 | * 1/2016 |

OTHER PUBLICATIONS

Heo et al., Titanium dental implants surface-immobilized with gold nanoparticles as osteoinductive agents for rapid osseointegration, Journal of Colloid and Interface Science, vol. 469, pp. 129-137, May 2016 (Year: 2016).*
International Search Report and Written Opinion for International application No. PCT/KR2019/005501, Aug. 16, 2019, ISA/KR.
Yi, Changing et al., Gold Nanoparticles Promote Osteogenic Differentiation of Mesenchymal Stem Cells through p38 MAPK Pathway, ACS NANO., Oct. 28, 2010, pp. 6439-6445, vol. 4, No. 11.
Sivanesan, A. et al., Electrncatalytic oxidation of ascorbic acid using a single layer of gold nanoparticles immobilized on 1,6-hexanedithlol modified gold elecuode, Electrochinnca Acta., Jul. 18, 2007, p. 8118-8124, vol. 52, Issue 28, Retrieved from <DOI: 10.1016/j.elec1acta.2007 07.020>.

* cited by examiner

*Primary Examiner* — Lezah Roberts
(74) *Attorney, Agent, or Firm* — ArentFox Schiff LLP

(57) ABSTRACT

The present invention provides surface-modified medical implants having one of more layer of gold nanoparticles, wherein, for example, the surface of a medical implant body could be immobilized with a single of double layers of GNPs. The implants could have a superior biocompatibility and superior osteogenic differentiation.

15 Claims, 22 Drawing Sheets

Specification includes a Sequence Listing.

TiHA 50.02° ± 3.83

1.TiO$_2$ 59.16° ± 2.07

2. TiOH 46.13° ± 4.37

3.TiSH 90.98° ± 7.62

5. TiGNP1-SH 46.81° ± 3.39

6. TiGNP2

42.58° ± 3.35

Scale bar: 500 μm

TiHA

1. $TiO_2$

2. TiOH

3. TiSH

4. TiGNP1

5. TiGNP1-SH

6. TiGNP2

Size: 20 × 20 μm

FIG. 11A
FIG. 11B
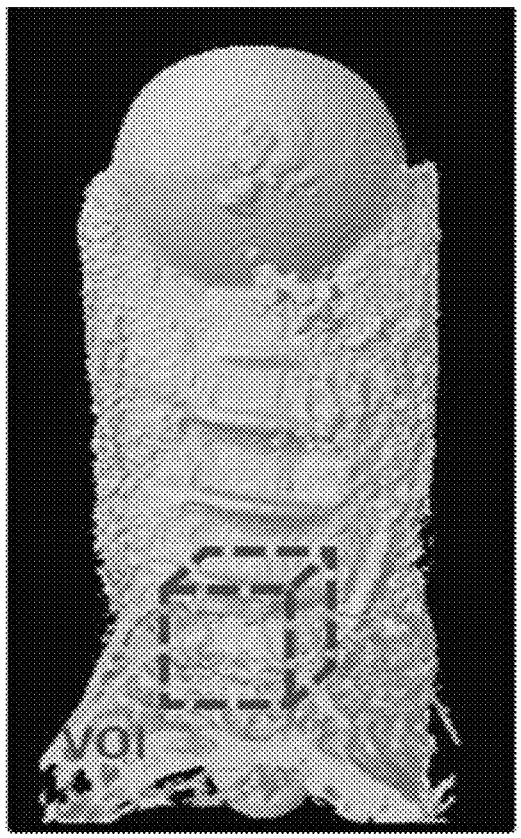
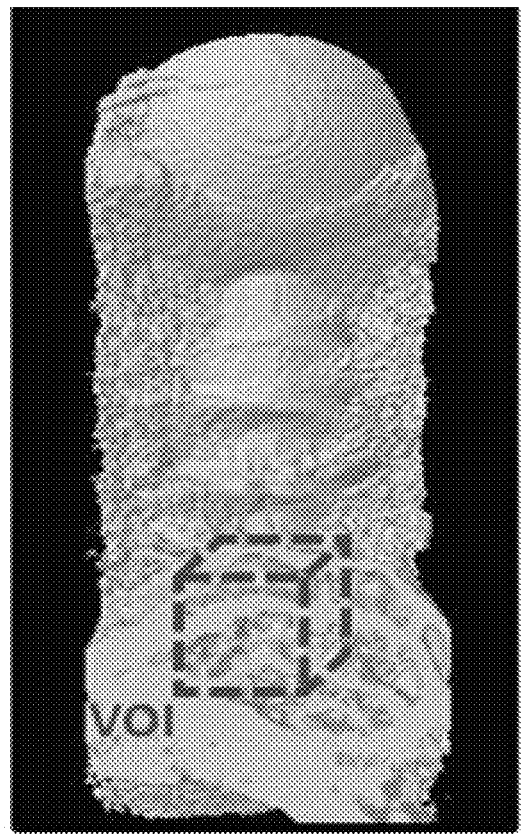

MEDICAL IMPLANTS CONTAINING SURFACE MODIFIED WITH GOLD NANOPARTICLES

CROSS-REFERENCE TO RELATED APPLICATIONS

This application is a continuation-in-part of PCT/KR2019/005501, filed May 8, 2019, which claims the benefit of priority from Korean Patent Application No. 10-2018-0052793, filed May 8, 2018 and Korean Patent Application No. 10-2019-0042182, filed Apr. 10, 2019, the contents of each of which are incorporated herein by reference.

TECHNICAL FIELD OF THE INVENTION

This invention is related with medical implants modified with gold nanoparticles.

BACKGROUND OF THE INVENTION

There are multiple types of medical implants such as dental, orthopedic, and cardiovascular implants in a bioinert implant market. The medical implants are made with several materials such as metals, polymers, and ceramics.

To increase the osteointegration between bones and inserted implants after the inserting process, multiple surface-modified titanium (Ti) and Ti alloy implants have been developed. Several methods, including (1) hydroxyapatite (HA), the calcium phosphate ceramic coated implants to prevent the release of metal ions and to enhance the biocompatibility and mechanical strength, (2) physically modified implants for the rough surface, (3) blasting method using ceramics for the rough surface, and (4) chemical etching such as $H_2SO_4$ and HCl for the rough surface, have been studied for the enhanced osteointegration. In dental fields, surface-modified implants with bioactive materials have been investigated to enhance the osteointegration between bones and a dental implant.

However, above methods are quite passive technics according to a physical enhancement due to an increase of surface area. In addition, much time and high prices are needed for the process. The instability within inserted areas is also an important issue.

To enhance the osteointegration, surface modified implants with active materials need to be developed for stronger osteointegration and biocompatibility.

SUMMARY OF THE INVENTION

The present invention provides a surface-modified medical implant with one of more layer of gold nanoparticles attached to the surface of the implant body.

The present invention also provides a method of improving osteointegration and osteogenic differentiation between inserted implants and bones.

The present invention further provides a method for preparing a surface-modified medical implant with one or more layer of gold nanoparticles.

DETAILED DESCRIPTION OF THE INVENTION

Figure 1A:
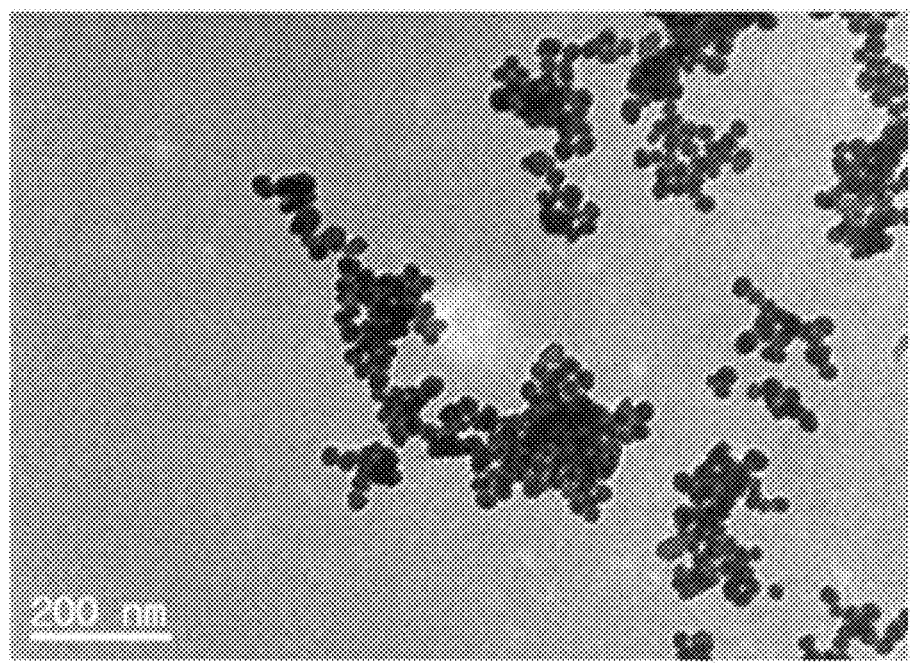
FIG. 1A and FIG. 1B provide a visual image using transmission electron microscopy (FIG. 1A, TEM, H-7100, Hitachi, Japan) and ultraviolet UV-visible spectrophotometer (FIG. 1B, UV-1650PC, Shimadzu, Japan) of synthesized spherical GNPs.

The present invention provides a medical implant bodies immobilized with single or double layers of GNPs on the surface.

In the present invention, the definition "medical implant" includes a substitute which could recover the loss of human tissues. The temporary or permanent medical equipment or devices to prevent or treat a medical disorder for mammals also may be included the "medical implant". The above-described "medical implant" may also include the optional remaining materials within inserted areas such as subcutaneous tissues, percutaneous tissues, an artery, a vein, a ventricle, an atrium, inner cavities, and organ tissues.

The above-described medical implant body may be biocompatible materials such as Ti, Ti alloy, stainless steel, nitinol, platinum, iridium, niobium, tantalum, gold, silver, UHMWPE (Ultra High Molecular Weight Polyethylene), PEEK (polyether ether ketone), polyurethane, silicone elastomer, bioresorbable polymer, alumina, zirconium, physiological active glass fiber, silicone nitrogenous compound, calcium phosphate, and carbon titanium. Specifically, Ti and Ti alloy have easy manufacturing process. In addition, they are relatively lighter than other metals and have a superior biocompatibility and corrosion resistances.

In the present invention, the term "gold nanoparticles (GNPs)" means that a material has been widely used in drug delivery system, biosensing, and tissue engineering areas due to the superior biocompatibility.

The above-described GNPs may include multiple shapes such as solid nanoparticles, nano-shell, nanocages, nanowire, and nanotubes.

The above-described GNPs can be purchased or synthesized as a manufacturing method. They are not limited to GNPs which can be spontaneously immobilized on a thiol group.

The above-described GNPs could induce an osteogenic differentiation after the endocytosis into cells.

The above-described GNPs have no cytotoxicity. Therefore, there is no side effect after the insertion into human tissues.

The size of above-described GNPs can be 10~100 nm, 50~100 nm, 10~80 nm, 25~60 nm, or 30~50 nm. The above-described size is facilitated for endocytosis of many GNPs into a cell.

The above-described medical implants could have a single or multiple layer of GNPs on the surfaces. Specifically, the above-described single layer of GNPs can be formed between thiol groups on the implant body and GNPs.

The above-described thiol group on the implant body could be formed by publicly known manufacturing methods. For example, the oxide membrane (02 membrane) of an implant surface could be sequentially modified with 12-Mercaptododecylphosphonic acid (MDPA), alkali, and silane. In detail, the hydroxy-end group on the implant surface can be reduced with alkali. After that process, hydroxy-end groups of the implant surface can be connected with silane using a thiol linking.

The above-described alkali during the surface-modifying step is not limited to —OH forming compounds using reduction methods of $O_2$ membrane. In the present invention, above alkali can be a NaOH.

The above-described silane for the modifying from —OH to —SH on the implant surface is not limited in a specific compound. For example, the above-described silane could be a thiolsilane having thiol groups such as (3-merchaptopropyl) trimethoxysilane.

The single layer of GNPs on the surface of implants could be spontaneously formed by the reaction between thiol groups of the implant surface and GNPs.

The above-described medical implants could have single or double layers of GNPs. Specifically, the connection between the single layer of GNPs and double layers of GNPs could be resulted from thiol groups on the single layer of GNPs.

The above-described thiol group on the single layer of GNPs could be formed using multiple compounds. For example, the compound can be a 12-MDPA. The single layer of GNPs on the implant surface can connect with alcohol solution including thiol groups.

The above-described alcohol for the forming of —OH on the single layer of GNPs is not limited in a specific compound. For example, the above-described alcohol can be an anhydrous alcohol.

The above-described thiol for the modifying from —OH to —SH on the single layer of GNPs is not limited in a specific compound. For example, the above-described thiol can be an 1,6-hexanedithiol.

The double layers of GNPs could be spontaneously formed by the connection between thiols on the single layer of GNPs and freshly added GNPs.

Using the above sequential steps, multiple layers of GNPs could be formed on the surface of implants. The above-described medical implant demonstrates various properties due to the double layers of GNPs.

The contact angle between a water drop and a medical implant could be 40~45°, 41~44°, or 42~43°. The above-described contact angle could have a superior hydrophilic property. The superior hydrophilic property could facilitate the migration of cells within the surface of implants.

The above-described medical implant may be an enhanced implant to induce the osteointegration when inserted into bones.

When an element measurement of the above-described surface of medical implants is performed, the surface could have oxygen ranges of 45~50%, carbon ranges of 15~20%, sulfur ranges of 3~8%, silicone ranges of 1~5%, or gold ranges of 2~4%. The above-described element measurement could be performed using x-ray photoelectron spectroscopy (XPS) equipment (K-Alpha+ spectrometer, Thermo Fisher Scientific, East Grinstead, UK).

In the present invention, the term "osteogenesis" or "osteogenic differentiation" means a process. The process occurs when several types of cells such as osteoblasts, osteoprogenitors, stem cells, and pre-osteoblasts are contributed to the growth of fresh bones within the inserted implant area. Cells or cell clusters also could be differentiated to mature osteoblasts. In that case, the differentiation is "osteogenesis".

The above-described medical implant could include a dental implant, cardiac pacemaker, stent, vascular grafts, brain pacemaker, artificial heart, port catheter, orthopedic implant, visual implant, retina, vitreous, cornea, skull base reconstruction, alternative bone substitute, phallus prosthesis, sphincteric muscle prosthesis, cochlear implant, catheter, urethra catheter, breathing hose, vein catheter, or canular. Specifically, dental or orthopedic implants could be included.

The above-described orthopedic implant can be a spinal implant, hip joint implant, pedicle screw, clavicle bone implant, pedicle screw, shoulder implant, elbow implant, intervertebral disc implant, finger joint implant, ankle implant, toe joint implant, knee joint implant, subtalar joint implant, lumbar implant, bone fusion implant, radial head implant, implant anchor pin, cranial implant, correction wedge, angle implant, implants for fracture (proximal tibia fracture), implant for metatarsal surgery, or posterior implant for foot surgery. The orthopedic implants are not limited in above-listed implants.

The above-described medical implants are suitable for bioinert implants. The implants have a superior biocompatibility and non-cytotoxicity. In addition, the osteointegration could be enhanced after the insertion into a human body. Therefore, the medical implants could be used as dental implants for bone forming or orthopedic implants.

In other aspect; is provided a surface-modifying methods comprising, including a thiol group exposure-step and a single layer of GNPs forming step by conjugating between at least partial on the surface of an implant body and a single layer of GNPs; double layers of GNPs forming step by conjugating between thiol groups of a single layer of GNPs and fresh added GNPs.

The above-described thiol group exposure-step within at least partial on the surface of an implant body could include sequential modifying steps using alkali or silane.

The above-described methods, thiol group exposure-step within at least partial on a single layer of GNPs could include sequential modifying steps using alkali or silane.

According to the above-described aspects, the medical implants could be immobilized with GNPs at least as double layers and have the effects such as superior biostability and superior osteogenic differentiation.

EXAMPLES

Hereinafter, preferred and experimental examples for helping understand the present invention will be suggested. The scope of the present invention is not limited to the following contents. The contents could be modified within a fundamental range of the present invention.

Example 1. Manufacture of GNPs

Thirty nanometer size of spherical GNPs are synthesized using a publicly known method (Huang, Xiaohua. Gold nanoparticles used in cancer cell diagnostics, selective photothermal therapy and catalysis of NADH oxidation reaction. Diss. Georgia Institute of Technology, Apr. 12, 2006). The specific method is as follows.

100 mL of $HAuCl_4$ solution (0.04 g $HAuCl_4.3H_2O$ (99.999%, #254169, Sigma Aldrich (Sigma, St. Louis, MO, USA)) in 100 mL deionized water (DW, 18.2 MΩ)) was refluxed (110° C., 800 RPM) for 1 hour in a 250 mL of two-neck flask, and then 600 μl of 38.8 mM trisodium citrate solution was quickly added. The color of the solution changed from yellow to black and to deep red. After the color changed, the solution was refluxed for an additional 15 min, and then the solution was stirred until it reached room temperature. Afterwards, GNPs solutions were filtered (0.22 μm, Millipore Carrigtwohill, Ireland) prior to usage in all experiments. The GNP solution including 30 nm of GNPs was stored in 4° C. of condition.

Figure 1B:
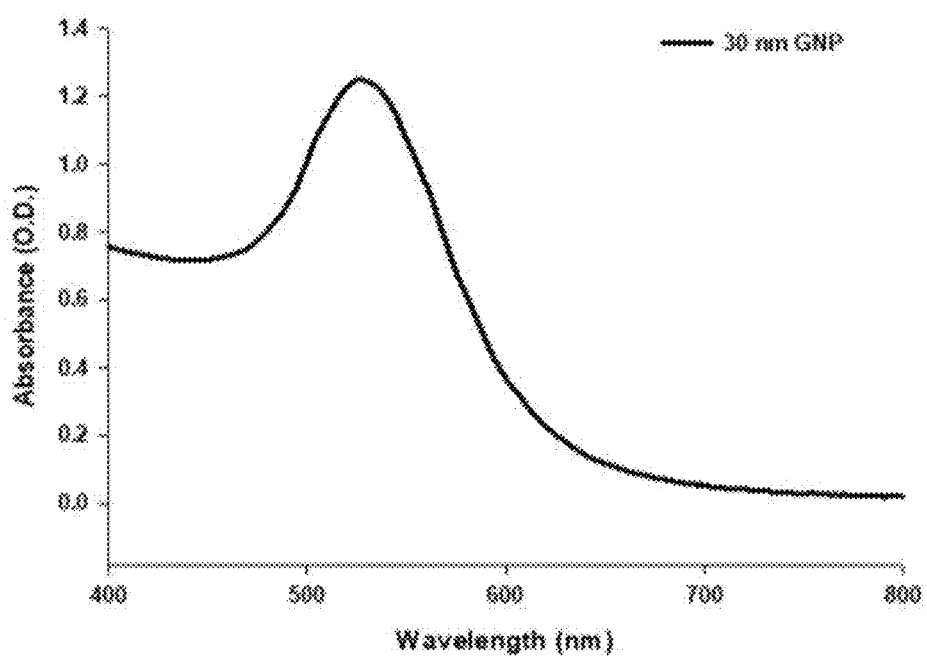
Figure 2A:
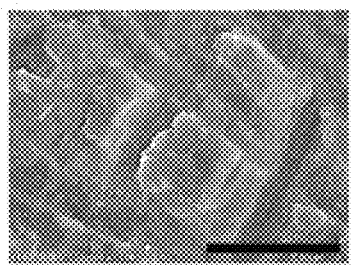
FIG. 2A, FIG. 2B, FIG. 2C, FIG. 2D, FIG. 2E, and FIG. 2F provide two-dimensional (2D) of visual images using scanning electron microscopy (SEM, S-4700 device, Hitachi, Japan) and values of water contact angle using video contact angle instrument (Phoenix 150, SEO, Korea) during the modifying process of the implant surfaces for an experiment example 1.
Figure 2B:
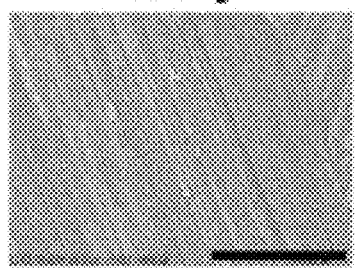
Figure 2C:
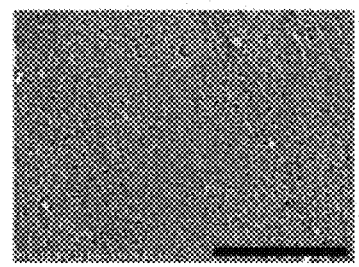
Figure 2D:
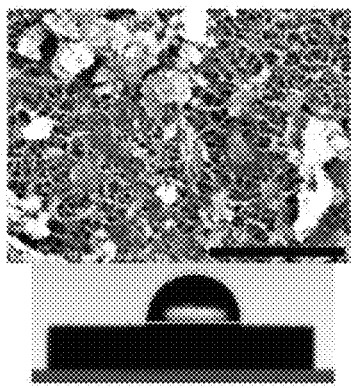
Figure 2E:
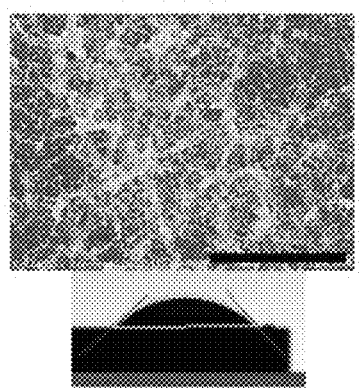
Figure 2F:
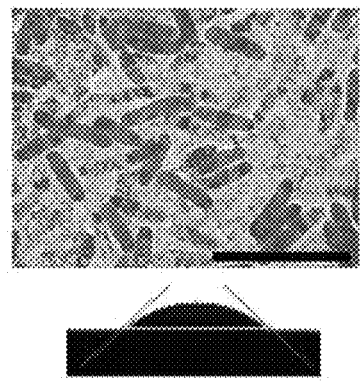
Figure 3A:
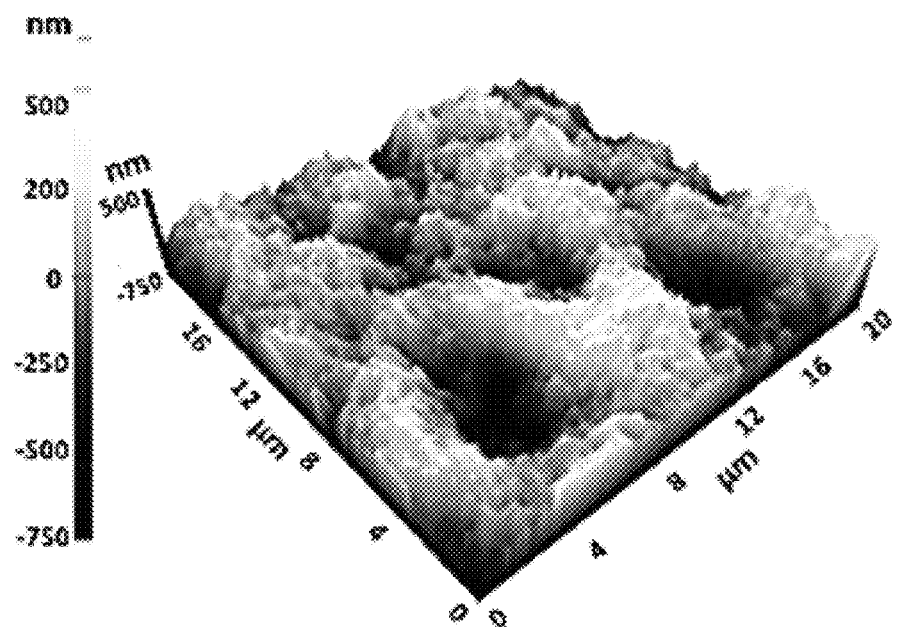
FIG. 3A, FIG. 3B, FIG. 3C, FIG. 3D, FIG. 3E, FIG. 3F, and FIG. 3G provide three-dimensional (3D) visual images using atomic force microscopy (AFM, PUCOStation STD (NANOS, AFM system, NanoInk, Inc., USA) during the surface modification process of an implant from the Experiment Example 1.
Figure 3B:
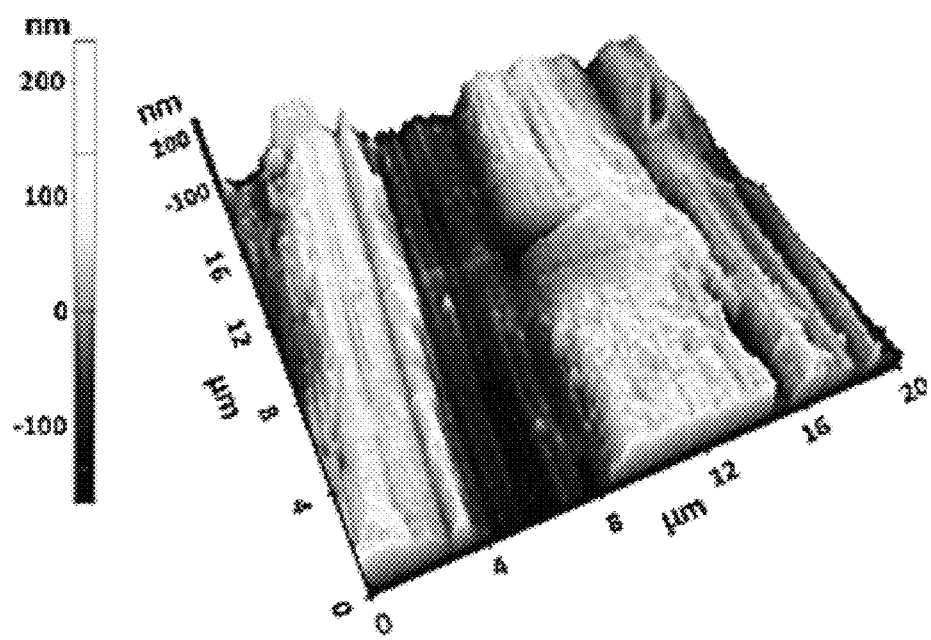
Figure 3C:
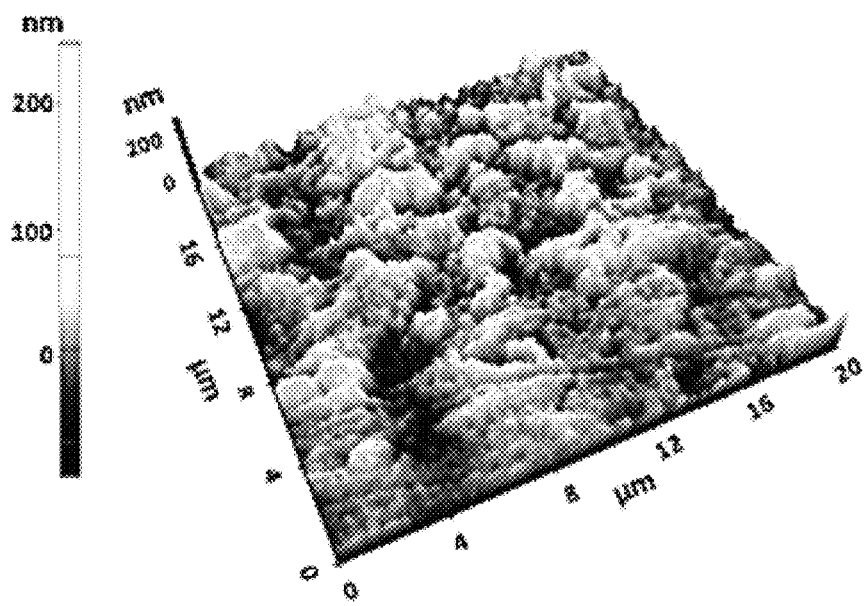
Figure 3D:
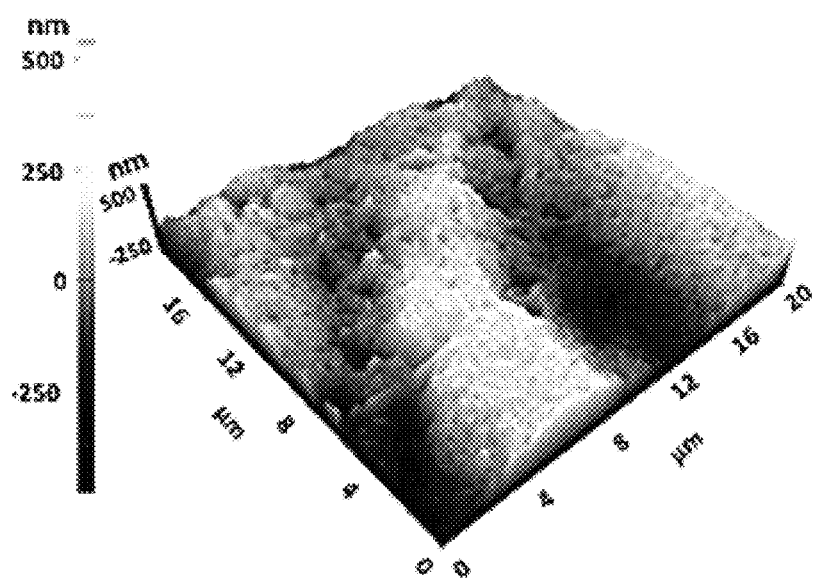
Figure 3E:
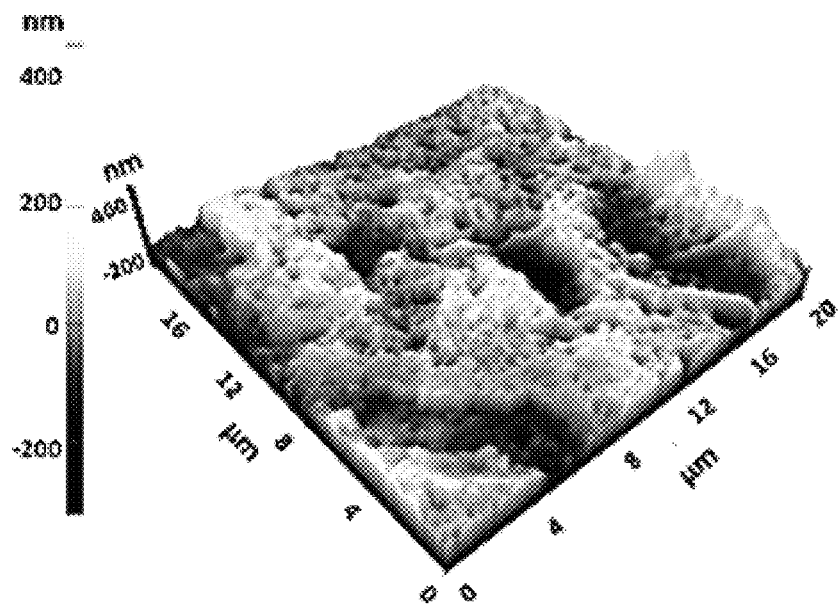
Figure 3F:
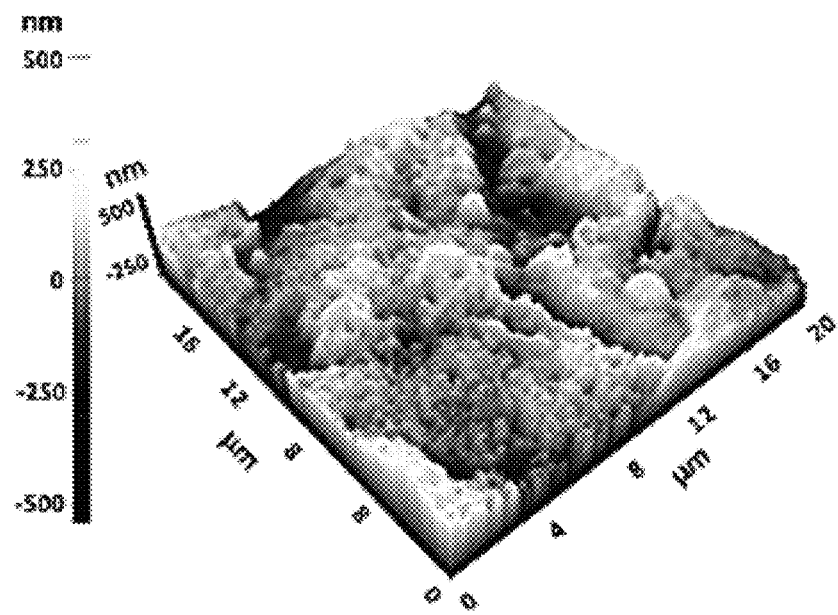
Figure 3G:
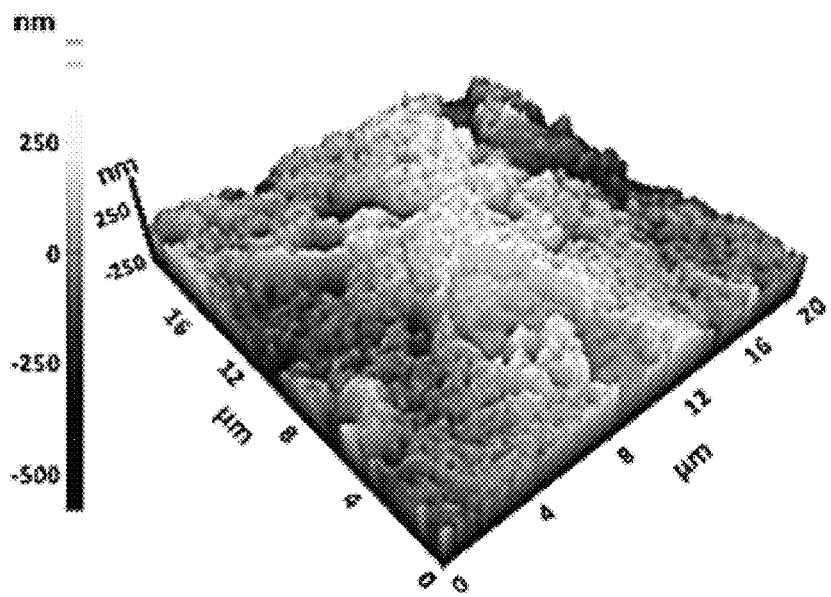

The manufactured GNPs were evaluated. FIG. 1 showed a visual image of synthesized spherical GNPs using TEM (left, H-7100, Hitachi, Japan) and wavelength data using UV-visible spectrophotometer (right, UV-1650PC, Shimadzu, Japan).

As shown in FIG. 1, the peak wavelength is 522 nm. The result showed the GNPs are successfully synthesized.

Example 2. Manufacture of Ti Disks Immobilized with GNPs

The GNPs immobilizing method between above-described GNPs and $TiO_2$ disks is as follows.

2.1. Preparation of $TiO_2$ Disks

The raw material of Ti metal was obtained from Medyssey, Co, Ltd (Seoul, Korea, Grade 4, https://www.medyssey.com/). The Ti disks (shape: cylinder) having a $O_2$ membrane were prepared (labeled as "$TiO_2$", diameter: 8 mm, thickness: 1 mm). The $TiO_2$ disks were ultrasonically cleaned three times in n-hexane, acetone, ethanol and DW for 20 min each and then dried under a $N_2$ stream for the experiments.

2.2. First Modification of Surfaces—Manufacture of TiOH Disks

Above manufactured (2.1.) cleaned $TiO_2$ disks were immersed in a 5 N NaOH solution (in a two-neck flask) to form active OH groups on the surface at 60° C. for 24 h (800~1000 RPM with magnetic bar).

The TiOH disks were ultrasonically cleaned five times in DW for 10 min each and then dried at 60° C. for 24 h.

2.3. Second Modification of Surfaces—Manufacture of TiSH Disks

In the second procedure, TiOH disks were immersed in a 2% (3-Mercaptopropyl) Trimethoxysilane (3-MTPMS, #175617, Sigma) of anhydrous toluene solution (99.8%, #244511, Sigma) to form active SH groups on the TiOH surface at 60° C. for 24 h (100 RPM with magnetic bar).

The TiSH disks were washed three times (10 min each) with anhydrous toluene, ethyl alcohol (anhydrous, special grade, SAMCHUN (Seoul, Korea)), and DW, then dried at 60° C. for 24 h (labeled as "TiSH").

2.4. Third Modification of Surfaces—Manufacture of a Single Layer of GNP Immobilized Disks (TiGNP1)

The above manufactured TiSH disks (2.3.) were immersed in above manufactured GNP solution (2.1) to immobilize a single layer of GNPs in a 37° C. of incubator (with 140 RPM) for 48 h (labeled as "TiGNP1").

The TiGNP1 disks were washed three times (10 min each) with DW using shaker, and then dried at 60° C.

2.5. Fourth Modification of Surfaces—Immobilizing of Active Thiol Group (—SH) to the Single Layer of GNP for the Manufacture of TiGNP1-SH Disks To immobilize double layers of GNPs on the above manufactured (2.4.) TiGNP1 disks, active SH groups on the surface of the single layer of GNPs were exposed as follows. TiGNP1 disks were immersed in a 10 mM 1,6-hexanedithiol (#H12005, Sigma) with ethyl alcohol solution (SAMCHUN) at 60° C. for 48 h (with 140 RPM) to form active SH groups again on the surfaces (labeled as "TiGNP1-SH").

The TiGNP1-SH disks were washed three times (10 min each) using shaker with ethyl alcohol (SAMCHUN), DW, and then dried at 60° C. for 24 h.

2.6. Fifth Modification of Surfaces—Manufacture of Double Layers of GNP Disks (TiGNP2)

The above manufactured TiGNP1-SH disks were immersed in above manufactured GNP solution (2.1) to immobilize double layers of GNPs on the surface at a 37° C. incubator (with 140 RPM) for 48 h (labeled as "TiGNP2").

The TiGNP2 disks were washed three times (10 min each) with DW using shaker, and then dried at 60° C. for 24 h.

Comparative Example 1. Modification of
Surfaces—Manufacture of HA Coated Titanium
Disks (TiHA)

As control groups, HA coated $TiO_2$ disks were manufactured. The HA is well known for the superior osteointegration ability. The HA was physically coated on the surface of $TiO_2$ disks by a Dentis device (Dentis Implant Co., Daegu, Korea) using a blasting method (Surface characteristics of a novel hydroxyapatite-coated dental implant. J Periodontal Implant Sci 2012; 42(2):59-63) (labeled as "TiHA").

Experimental Example 1. Surface Analysis of
Modified Ti Disks with GNPs 1.1. Analysis of Hydrophilic Property and 2D-Structure on Ti Surfaces The hydrophilic property on the surface of the bioinert implant is important for the migration of cells. For example, as the hydrophilic property of the surface increases, the migration of cells increases. We compared the hydrophilic property and 2D-structure between TiGNP2 and TiHA disks.

The 2D-structure of the surface was evaluated by SEM (S2300, Hitachi, Japan, ×10,000). The contact angle between a water drop and the surface of a disk was evaluated as a parameter of the hydrophilic property. FIGS. 2A-2F provide 2D-visual images (up, scale bar: 500 μm) and contact angles (down) of TiHA, $TiO_2$, TiOH, TiSH, TiGNP1, TiGNP1-SH, and TiGNP2 disks.

As the contact angle between a water drop and the surface of a disk decreases, the hydrophilic property increases (FIGS. 2A-2F).

As the contact angle of TiHA, $TiO_2$, TiOH, TiSH, TiGNP1-SH, and TiGNP2 was 50.02°±3.83, 59.16°±2.07, 46.13°±4.37, 90.98°±7.62, 47.27°±2.87, 46.81°±3.39, and 42.58°±3.35, respectively (FIGS. 2A-2F).

The contact angle of TiGNP1 and TiGNP2 is lower than that of TiHA. Specifically, TiGNP2 have the lower contact angle among the Ti groups.

1.2. Analysis of 3D-Structure on Ti Surfaces

The 3D-structure of the Ti surface was evaluated by AFM (PUCOStation STD, NANOS AFM system, NanoInk, Inc., USA).

FIGS. 3A-3G provide 3D-visual images of TiHA, $TiO_2$, TiOH, TiSH, TiGNP1, TiGNP1—SH, and TiGNP2 disks.

As shown in FIGS. 3A-3G, the surfaces of all Ti disk groups were visualized.

1.3. Component Analysis on the Ti Surface

Atomic chemical compositions on the surfaces of TiHA, $TiO_2$, TiOH, TiSH, TiGNP1, and TiGNP2 were analyzed by XPS (K-Alpha, Thermo Scientific, UK) analysis. Table 1 provides the percentages (%) of atom concentration.

TABLE 1

| | XPS atomic concentration (%) | | | | | | |
|---|---|---|---|---|---|---|---|
| | Ti | O | C | S | Si | Au | P | Ca |
| TiHA | 0.21 | 59.34 | 5.64 | — | — | — | 13.07 | 21.75 |
| $TiO_2$ | 25.94 | 49.68 | 23.83 | — | — | — | — | — |
| TiOH | 24.97 | 48.99 | 25.71 | — | — | — | — | — |
| TiSH | 18.67 | 53.27 | 19.85 | 2.74 | 5.44 | — | — | — |
| TiGNP1 | 24.6 | 54.27 | 12.96 | 4.79 | 1.53 | 1.85 | — | — |
| TiGNP2 | 19.94 | 49.5 | 19.18 | 5.66 | 2.18 | 3.55 | — | — |

Figure 4:
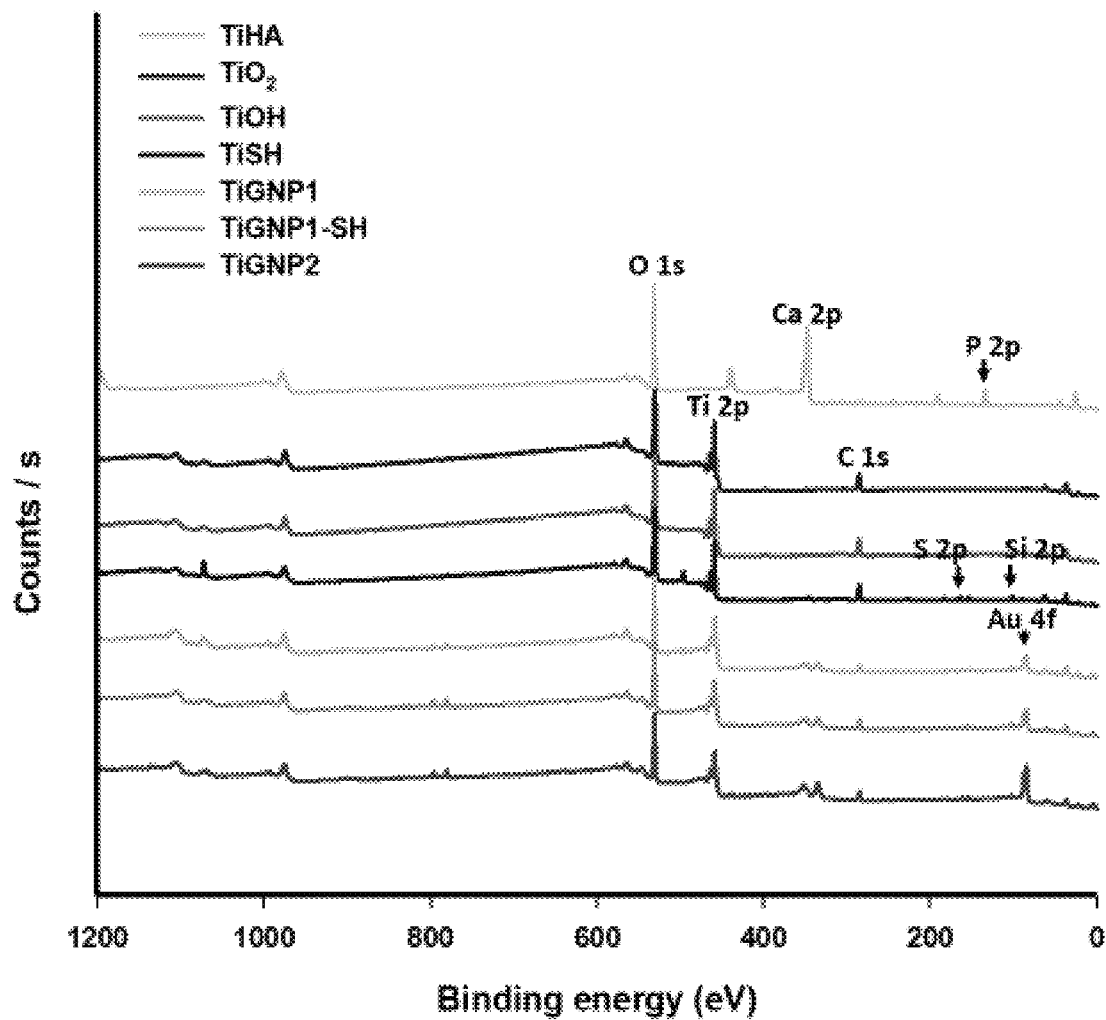
FIG. 4 provides the components on the surface during the modifying process of an implant for the experiment example 1. The XPS equipment was used for the analysis.

FIG. 4 provides the qualitative data of atomic chemical compositions on the surfaces of TiHA, $TiO_2$, TiOH, TiSH, TiGNP1, and TiGNP2 disks.

Table 1 and FIG. 4 indicate that the GNPs were successfully immobilized on the surface of Ti disks. Specifically, the Au % was increased in the TiGNP2 group than that of TiGNP1 group.

Experimental Example 2. Modification of Surfaces
and the Property Analysis—Manufacture of GNP
Immobilized Ti Disks The cell viability was analyzed in vitro as follows.

2.1. Analysis of the Cell Proliferation and Viability

To investigate whether Ti disks have cytotoxicity, we undertook live/dead staining and cell counting kit (CCK) assays for 48 h using human bone-marrow-derived mesenchymal stem cells (MSCs, FIGS. 5A-5F). The MSCs were obtained from Invitrogen (Carlsbad, CA, USA) and cultured on cell culture plates (Falcon Becton Dickinson (Falcon), Lincoln Park, NJ). Total five experimental groups were used for the cell toxicity and live and dead assays.

Group 1: The MSCs (Passage 6) were seeded on the cell culture plate and cultured with growth medium (GM, labeled as "plate")

Group 2: The MSCs (Passage 6) were seeded on the above-prepared $TiO_2$ disks and cultured with GM (labeled as "$TiO_2$")

Group 3: The MSCs (Passage 6) were seeded on the above-prepared TiHA disks and cultured with GM (labeled as "TiHA")

Group 4: The MSCs (Passage 6) were seeded on the above-prepared TiGNP1 disks and cultured with GM (labeled as "TiGNP1")

Group 5: The MSCs (Passage 6) were seeded on the above-prepared TiGNP2 disks and cultured with GM (labeled as "TiGNP2")

The growth medium was MesenPRO RSTM basal medium mixed with the MesenPRO RSTM growth supplement (Thermo Fisher Scientific, Rockford, IL, USA)). Passage 6 of the MSCs was carefully seeded at $5 \times 10^4$ cells in 80 μL on 24-well culture plates (Falcon) or disk surfaces for plate, $TiO_2$, TiHA, TiGNP1, and $TiGNP_2$ groups. They were allowed to adhere for two hours, after which 1 ml of GM was gently added to each well (n=4 per group).

The cell viability on the surfaces of the Ti disks was quantitatively evaluated using a cell counting kit (CCK-8, Dojindo Molecular Technologies Inc., Japan) after culture for 24 or 48 h, respectively (n=4 per group). At each predetermined time point, the GM was replaced with fresh GM containing CCK-8 (500 μL of 0.1 mL/ml). After incubation for 2 h, the absorbance was measured at 450 nm with a microplate reader (Bio-Rad, Hercules, CA, USA). The absorbance of each culture plate group at 24 or 48 h was fixed at 100% and the absorbance levels of the other groups were calculated relative to that level. Table 2 provides the result.

| | Average (%, after 24 h) | STDEV (after 24 h) | Average (%, after 48 h) | STDEV (after 48 h) |
|---|---|---|---|---|
| plate | 100 | 2.9 | 100.0 | 5.7 |
| $TiO_2$ | 108.3 | 2.2 | 103.7 | 4.2 |
| TiHA | 92.8 | 2.4 | 86.4 | 1.3 |

-continued

|  | Average (%, after 24 h) | STDEV (after 24 h) | Average (%, after 48 h) | STDEV (after 48 h) |
|---|---|---|---|---|
| TiGNP1 | 108.8 | 3.7 | 106.9 | 1.7 |
| TiGNP2 | 114.7 | 3.8 | 111.9 | 3.0 |

As shown in Table 2, all groups showed no cytotoxicity.

Figure 5:
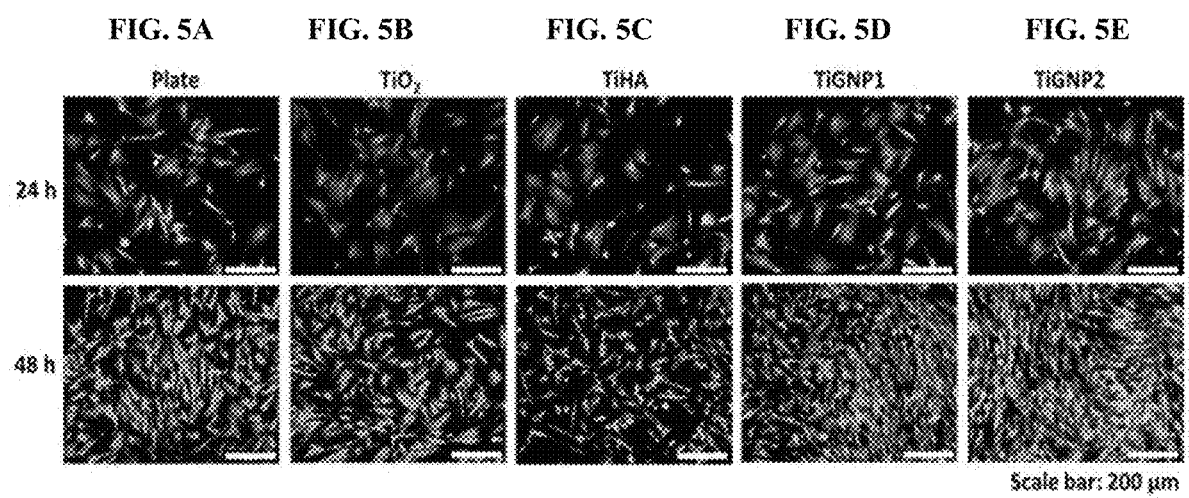
FIGS. 5A-5E provide qualitative visual images of the cell viability at 24 hours and at 48 hours.

As shown in FIG. 5, the MSCs in all groups were stained with green (alive) or stained with red (dead) for the qualitative cell-toxicity-evaluation. The visual images were observed at ×200 using an inverted fluorescence microscope (Olympus, IX71, Japan).

As shown in FIG. 5, all groups showed no cytotoxicity.

As shown in FIG. 5, the highest proliferation was observed at TiGNP2 group.

2.2 Analysis of the Osteogenic Differentiation from MSCs In Vitro

To evaluate the osteogenic differentiation of MSCs on Ti disk groups, passage 6 of MSCs were used for the following experiments. Total six of experimental groups were used for ALP and RT-PCR experiments.

Group 1: The MSCs were seeded on the cell culture plate and cultured with GM (labeled as "Plate (GM)")

Group 2: The MSCs were seeded on the cell culture plate and cultured with osteogenic medium (OM, labeled as "Plate (OM)")

Group 3: The MSCs were seeded on the above-prepared $TiO_2$ disks and cultured with OM (labeled as "$TiO_2$ (OM)")

Group 4: The MSCs were seeded on the above-prepared TiHA disks and cultured with OM (labeled as "TiHA (OM)")

Group 5: The MSCs were seeded on the above-prepared TiGNP1 disks and cultured with OM (labeled as "TiGNP1 (OM)")

Group 6: The MSCs were seeded on the above-prepared TiGNP2 disks and cultured with OM (labeled as "TiGNP2 (OM)")

The experiments related with osteogenic differentiation were performed using above 6 groups. Passage 6 of the MSCs was carefully seeded at $5 \times 10^4$ cells to a level of 80 μL on 24-well culture plates or Ti disks for plate (OM), $TiO_2$ (OM), TiHA (OM), TiGNP1 (OM), and TiGNP2 (OM) groups. The OM is dulbecco's modified eagle medium (DMEM, GIBCO, Grand Island, NY)) containing 10% fetal bovine serum (FBS, GIBCO), 1% penicillin-streptomycin (PS, GIBCO), 10 mM-β-glycerol phosphate (Sigma), 300 μM of ascorbic acid (Sigma), and 0.1 μM of dexamethasone (Sigma)). Afterwards, the MSCs were adhered for two hours, and 1 ml of GM or OM was then gently added to each well (n=4 per group). MSCs cultured with GM in 24-well plates were added for the plate (GM) group under identical conditions. All groups were incubated for 3, 7, or 14 days in each case.

The ALP activity assay for the evaluation of osteogenic differentiation was performed as follows.

The typical enzyme, ALP, is expressed during the osteogenic differentiation of MSCs. At each predetermined time interval, the seeded cells were washed with DPBS twice and then lysed using 1× RIPA buffer (50 mM Tri-HCL (pH 7.4), 150 mM NaCl, 0.25% deoxycholic acid, 1% NP-40 and 1 mM EDTA) with a protease inhibitor cocktail (Boehringer Mannheim GmbH, Germany) for 30 min on ice. Each of the lysates was centrifuged at $1.7 \times 10^4$ g at 4° C. for 15 min to remove the cell debris. After centrifugation, the supernatant was collected and then reacted with a p-nitrophenyl phosphate solution (pNPP, Sigma) in a 5% $CO_2$ humidified incubator at 37° C. for 30 min. The reaction with pNPP was then terminated by adding 50 of 1 N NaOH. The production of p-nitrophenol was measured at 405 nm using a microreader. A calibration curve was generated using standard p-nitrophenol solutions. The total quantity of the p-nitrophenol produced from the cultured cells was determined by comparing these results against a calibration curve. Finally, the enzyme activity was expressed in terms of the amount in μM of the reaction product (p-nitrophenol) per μg.

Figure 6:
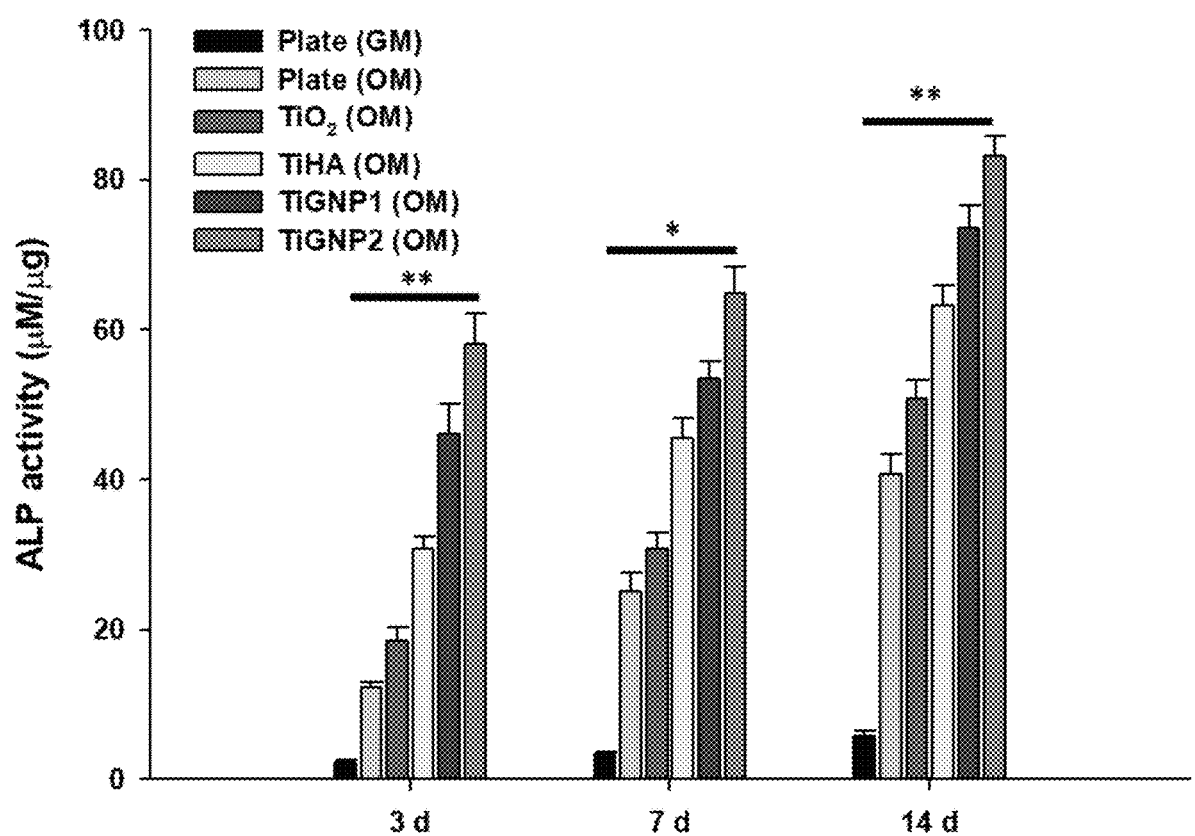
FIG. 6 provides values of the alkaline phosphatase (ALP) activity to compare the values of the osteogenic differentiation among experimental groups.

FIG. 6 provides the levels of the ALP activity for the comparison among all groups.

As shown in FIG. 6, ALP levels in TiGNP2 (OM) groups was constantly increased for 14 d. In addition, the highest level of ALP was observed at each time point in the TiGNP2 (OM) group.

Double layers of GNPs on the TiGNP2 disks significantly improved the osteogenic differentiation of MSCs more as compared to that by HA. This result indicates that bioinert implants having double layers of GNPs could induce the osteointegration after insertion into bones.

We performed qRT-PCR analyses to evaluate the osteogenic differentiation of MSCs on Ti disk groups. Typical genes related to osteogenic differentiation, COL1 and Runx2 and OPN, were investigated by qRT-PCR. COL1 is the most abundant protein in the bone matrix and usually is formed during the proliferation of osteoblast cells. Runx2 is the key osteogenic transcription factor. OPN induces calcium deposition in the extracellular matrix during its mineralization stage. For qRT-PCR at each predetermined time interval, the seeded cells of total RNA per group were extracted using Trizol reagent (Invitrogen) according to the manufacturer's instructions. Complementary DNA (cDNA) was synthesized from 1 μg RNA using a Maxim RT Premix kit (iNtRON Biotechnology, Inc., Korea). The qRT-PCR step was performed with an ABI Step-One real-time PCR system (Applied Biosystems, Warrington, UK). The reaction mixture consisted of the SYBR Green 2×PCR Master Mix (Applied Biosystems), a cDNA template, and forward/reverse primers. The relative expression levels of COL1, Runx2, and OPN were normalized to that of β-actin using the $2^{-\Delta\Delta CT}$ method. The primers were obtained from Bioneer (Daej eon, Korea). The primer sequences were as follows: COL1 (Forward: GAG GGC CAA GAC GAA GAC ATC (SEQ ID NO:1), Reverse: CAG ATC ACG TCA TCG CAC AAC (SEQ ID NO:2)), Runx2 (Forward: CCG ATG GGA CCG TGG TT (SEQ ID NO:3), Reverse: CAG CAG AGG CAT TTC GTA GCT (SEQ ID NO:4)), OPN (Forward: CAG TTG TCC CCA CAG TAG ACA C (SEQ ID NO:5), Reverse: GTG ATG TCC TCG TCT GTA GCA TC (SEQ ID NO:6)), β-actin (Forward: CGT AAA GAC CTC TAT GCC AAC A (SEQ ID NO:7), Reverse: CGG ACT CAT CGT ACT CCT GCT (SEQ ID NO:8)). The fold change of control group (Plate (GM)) at 3 days of culture was set at 1-fold and the ratio of the normalized fold change was calculated.

Figure 7:
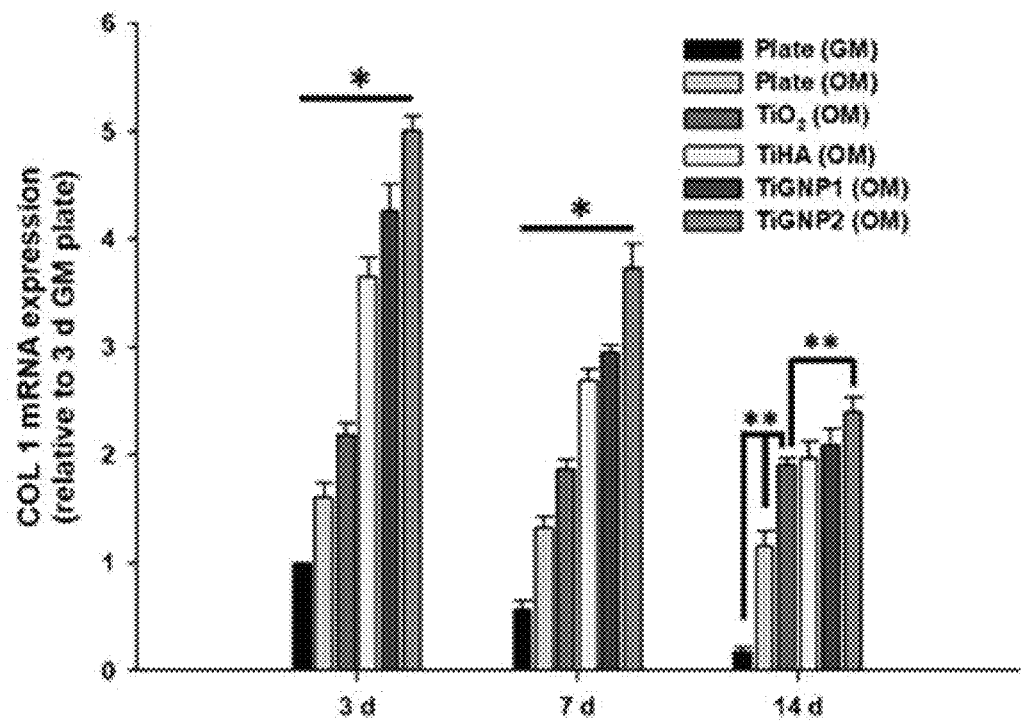
FIG. 7 provides the mRNA expression of collagen type 1 (COL1) using real-time polymerase chain reaction (qRT-PCR) to compare the osteogenic differentiation among experimental groups FIG. 8 provides the mRNA expression of runt-related transcription factor 2 (Runx2) using qRT-PCR to compare the levels of the osteogenic differentiation among experimental groups.

FIG. 7 provides the mRNA levels of COL1 in all groups after RT-PCR experiments.

Figure 8:
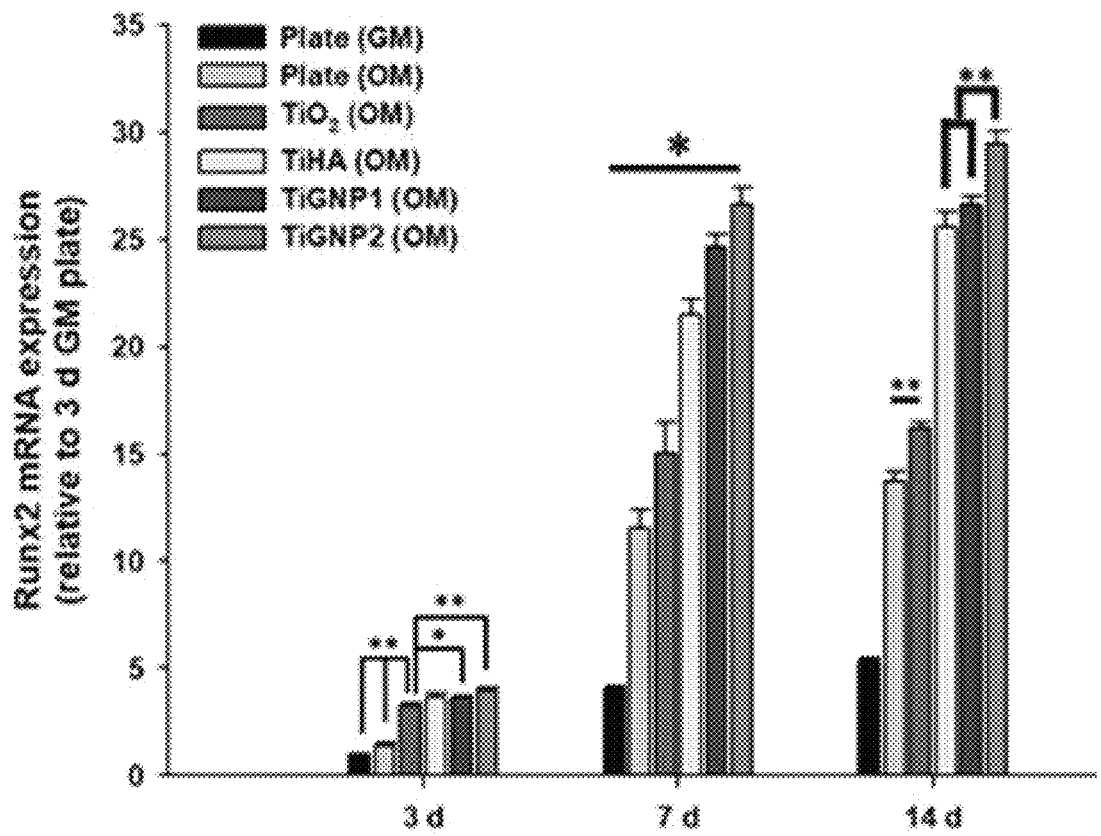

FIG. 8 provides the mRNA levels of Runx2 in all groups after RT-PCR experiments.

Figure 9:
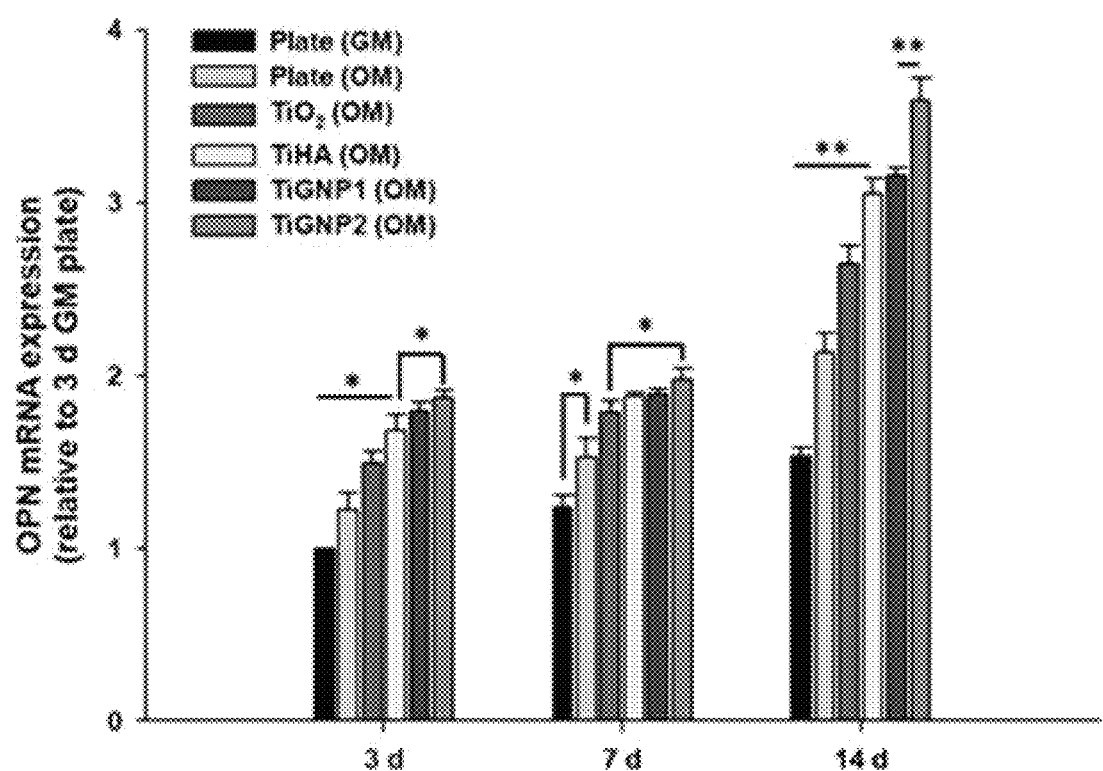
FIG. 9 provides the mRNA expression of osteopontin (OPN) using qRT-PCR to compare the osteogenic differentiation among experimental groups.

FIG. 9 provides the mRNA levels of OPN in all groups after RT-PCR experiments.

As shown in FIGS. 7-9, The mRNA levels in TiGNP2 (OM) groups were constantly increased for 14 d. The highest mRNA level for COL1, Runx2, and OPN was observed at each time point in the TiGNP2 (OM) group.

This result indicates that bioinert implants having double layers of GNPs could induce the osteointegration after insertion into bones.

Experimental Example 3. Analysis of the Osteointegration In Vivo

The osteointegration was analyzed in vivo as follows. Four New Zealand female white rabbits weighing between 4.0 and 4.2 kg were purchased from Orient Bio Inc. (Seongnam, Korea). They were housed individually in cages under the following conditions: room temperature (20-23° C.), 55% humidity, 12 h circadian light rhythm, and free access to water/food. Twenty-four Ti pedicle screws were used for in vivo study. Twelve screws were HA coated ones and the other twelve were double layers of GNP immobilized screws. Two groups of screws were inserted into a vertebra of the rabbit for in vivo evaluation.

Group 1: HA was coated on the surface of $TiO_2$ pedicle screw (labeled as "HA screw").
Group 2: Double layers of GNPs were immobilized on the surface of $TiO_2$ pedicle screw (labeled as "GNP2 screw").

$TiO_2$ pedicle screws were also obtained from medyssey, co, Ltd. The screws of group 1 had a diameter of 3.0 mm, a length of 9.0 mm, and a thread pitch of 1.5 mm. The HA coating method for the HA screws is same as that for the TiHA disk (above Example 2.1. described). The HA screws were used for a positive control group. The screws of group 2 also had a diameter of 3.0 mm, a length of 9.0 mm, and a thread pitch of 1.5 mm. The double layers of GNP immobilizing method for the GNP2 screws is same as the immobilizing method for the TiGNP2 disk (above Example 2.1. described). Six screws (HA screws=3, GNP2 screws=3) were alternately implanted in each rabbit.

Above-described two groups of screws were inserted in two types of rabbit models.

Model 1: OVX model, two rabbits were bilaterally ovariectomized and six screws (HA screws=3, GNP2 screws=3) were alternately implanted in each rabbit (n=6).
Model 2: SHAM model, two rabbits were non-ovariectomized (same condition except for the ovariectomizing process) and six screws (HA screws=3, GNP2 screws=3) were alternately implanted in each rabbit (n=6).

The anesthetizing drug (Zoletil® (50 mg/kg, Virbac Laboratories, France)/Rompun® (10 mg/kg, Bayer, Korea)) solution was intraperitoneally administered to the animals. Anesthesia was established within 15-20 minutes and the anesthesia was maintained with isoflurane (3%) in oxygen (2 L/minute) via a facemask. Two rabbits were bilaterally OVX for the OVX models and the other two rabbits were used for the SHAM models. After the surgeries, the animals were examined daily for activity, eating, and wound healing. Three months after the implanting operation, the rabbits were sacrificed using an overdose of KCl intravenously. Shortly after sacrificing the rabbits, vertebral blocks including screws were safely separated from the whole spine using a bone cutter for the evaluation of the osteointegration.

Three-Dimensional Measurements of Bone Parameters Using μCT

Shortly after sacrificing the rabbits, vertebral blocks (OVX: 1, SHAM: 1) including six screws (HA: 3, GNP2: 3) were safely separated from the whole spine using a bone cutter. The blocks were converted into digital imaging and communication in medicine (DICOM) files using μCT equipment (Quantum FX, Perkin Elmer, Waltham, MA, USA). All the screws in the vertebral blocks were reconstructed using computer tomographic volume (CTvol) software (https://www.bruker.com/service/support-upgrades/software-downloads/micro-ct/measurements-and-visualization.html, version: 2.3.2.0, Bruker Corporation, Billerica, MA, USA).

Figure 10A:
FIG. 10A and FIG. 10B provide the micro computed tomography (μCT) of visual images for the 3D analysis of a HA coated titanium screw (FIG. 10A: HA screw) and double layers of GNPs screw (FIG. 10B: GNP2 screw) after the insertion into ovariectomized (OVX) rabbit models FIG. 11A and FIG. 11B provide the μCT of visual images for the 3D analysis of the HA screws (FIG. 11A) and the GNP2 screw (FIG. 11B) after the insertion into SHAM rabbit models.
Figure 10B:
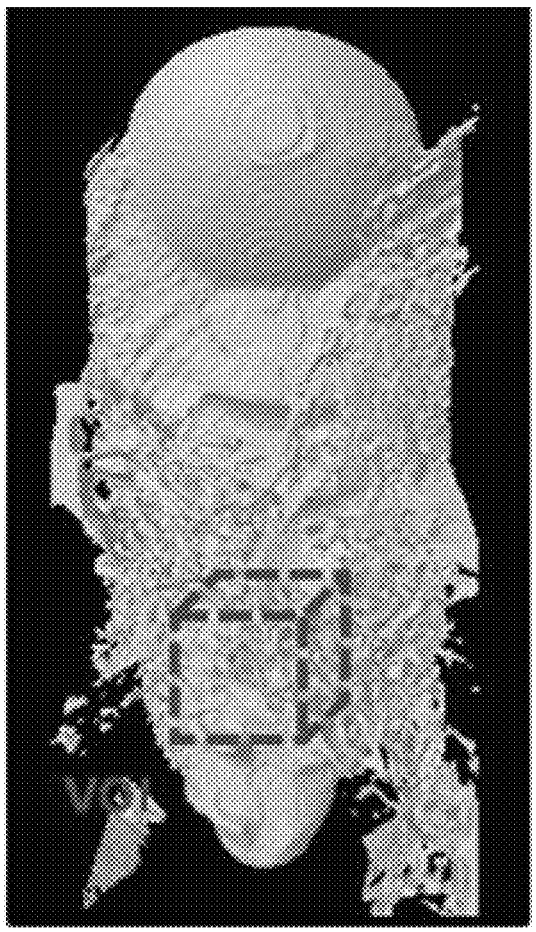

FIG. 10A and FIG. 10B provides the representative 3D images using μCT in an OVX model (left: HA screw, right: GNP2 screw)

FIG. 11A and FIG. 11B provides the representative 3D images using μCT in a SHAM model (left: HA screw, right: GNP2 screw)

BV/TV and BS/TV in the designated VOIs were quantified by volumetric analyzing using CT-Analyzer (CTAn) software (https://www.bruker.com/service/support-upgrades/software-downloads/micro-ct/measurements-and-visualization.html, version: 1.17.7.2+, Bruker). The VOIs included screws with the surrounding bones and tissues and were 3×3×3 $mm^3$ in size. VOIs were randomly designated for each screw. BV ($mm^3$)/TV ($mm^3$) in each VOI was demonstrated as a percentage and the BS ($mm^2$)/TV ($mm^3$) in each VOI was shown as 1/mm (n=3 per group). Table 3 and 4 provide the measured levels.

TABLE 3

|  | OVX model | | SHAM model | |
| --- | --- | --- | --- | --- |
| BV/TV (%) | HA screw | GNP2 screw | HA screw | GNP2 screw |
| N = 1 | 0.19 | 0.24 | 0.29 | 0.35 |
| N = 2 | 0.18 | 0.22 | 0.28 | 0.41 |
| N = 3 | 0.21 | 0.24 | 0.31 | 0.42 |
| Average | 19.33 | 23.08 | 29.32 | 39.27 |
| STDEV | 1.62 | 1.04 | 1.54 | 3.70 |

TABLE 4

|  | OVX model | | SHAM model | |
| --- | --- | --- | --- | --- |
| BS/TV (1/mm) | HA screw | GNP2 screw | HA screw | GNP2 screw |
| N = 1 | 6.27 | 7.81 | 8.62 | 9.48 |
| N = 2 | 6.73 | 8.04 | 8.25 | 9.40 |
| N = 3 | 6.33 | 7.38 | 8.49 | 10.41 |
| Average | 6.44 | 7.75 | 8.45 | 9.76 |
| STDEV | 0.25 | 0.34 | 0.19 | 0.56 |

Figure 12:
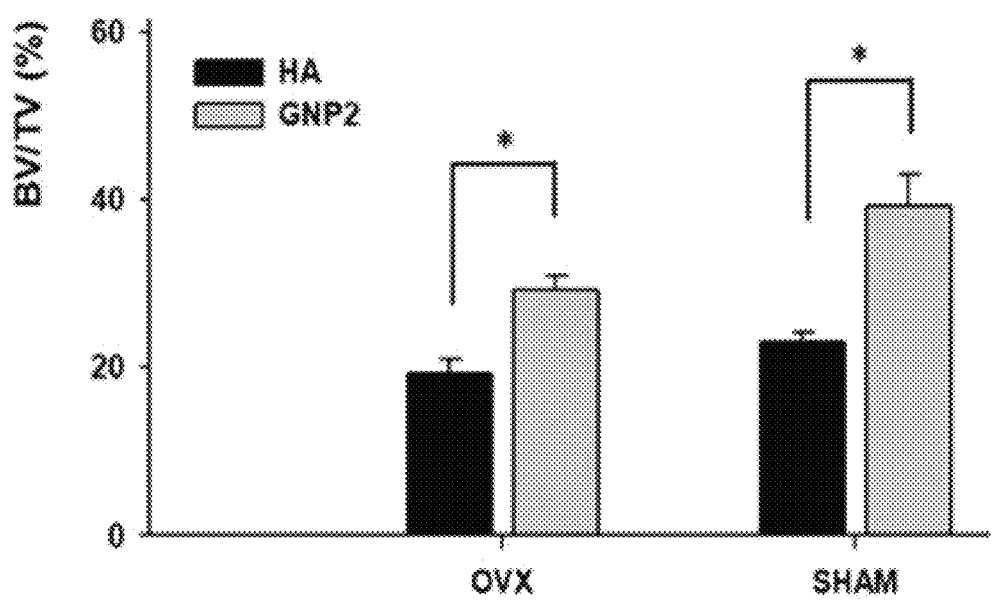
FIG. 12 provides the quantitative levels of bone volume (BV)/tissue volume (TV) within the designated volume of interests (VOIs) after the screw insertion into the OVX or SHAM rabbit model.

FIG. 12 provides the BV/TV percentages within the VOIs in the OVX and SHAM model (left: HA screw, right: GNP2 screw)

Figure 13:
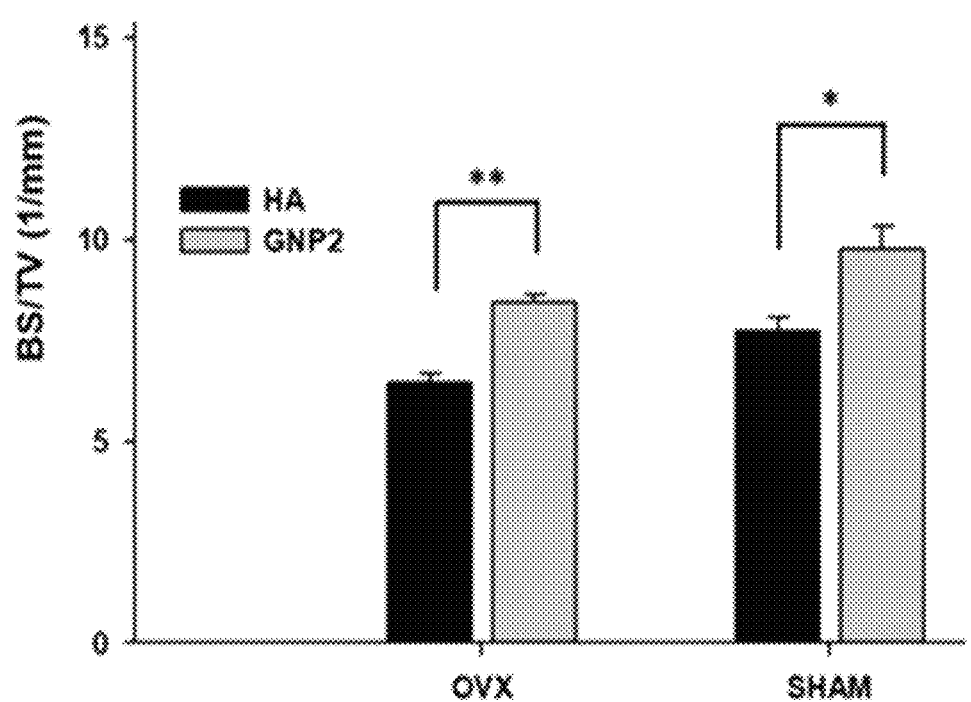
FIG. 13 provides the quantitative levels of bone surface (BS)/TV within the designated VOIs after the screw insertion of the screws into the OVX or SHAM rabbit models.

FIG. 13 provides the levels of BS/TV within the VOIs in the OVX and SHAM model (left: HA screw, right: GNP2 screw)

As shown in Table 3, 4 and FIGS. 12, 13, the BV/TV in the OVX models was significantly increased in the GNP2 group as compared to those in the HA group. The BS/TV values were significantly increased in the GNP2 group of both the OVX and the SHAM models.

This result indicates that double layers of GNPs immobilized screws induced the osteointegration between the inserted area and the implanted screw.

Histological Preparation and 2D Measurements of the Screws Using Masson-Goldner Trichrome Staining Shortly after sacrificing the animals, vertebral blocks (OVX: 1, SHAM: 1) including six screws (HA: 3, GNP2: 3) were also safely separated from the whole spine. The specimen blocks including each screw were fixed in 10% neutral buffered formalin (Sigma) for five days and were dehydrated with alcohol. The specimens including the screws were then embedded in resin (Technovit 7200 VLC, Kulzer, Germany). To display the screw and the surrounding tissues from the blocks, the blocks were grounded and sectioned parallel to the long axis of the screw using a water-cooled band saw. The sections were prepared with EXAKT grinding equipment (EXAKT 300, Norderstedt, Germany). The final thickness of the sections was 70 µm and the sections were stained with Masson-Goldner trichrome staining kits (Roth, Karlsruhe, Germany) according to the manufacturer's instructions. The stained images were evaluated using a light microscope (Olympus IX71). Two images at 40× magnification were randomly designated. A ROI (400×800 µm$^2$) was also randomly designated within the 40× magnification images. To depict the ROI images in detail, 100× magnification was used.

Figure 14A:
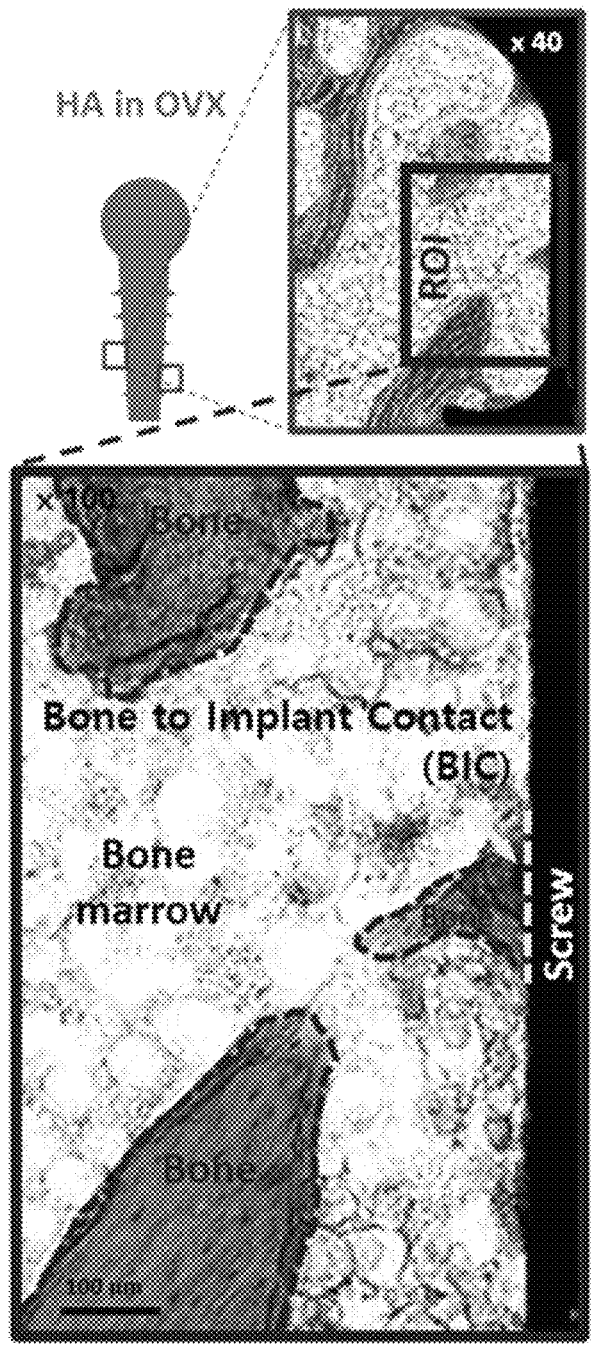
FIG. 14A provides the representative visual images within the designated region of interest (ROI) after the HA screw insertion into an OVX rabbit model.

FIG. 14A provides the representative 2D images in a HA screw group after Masson-Goldner trichrome staining in an OVX model.

Figure 14B:
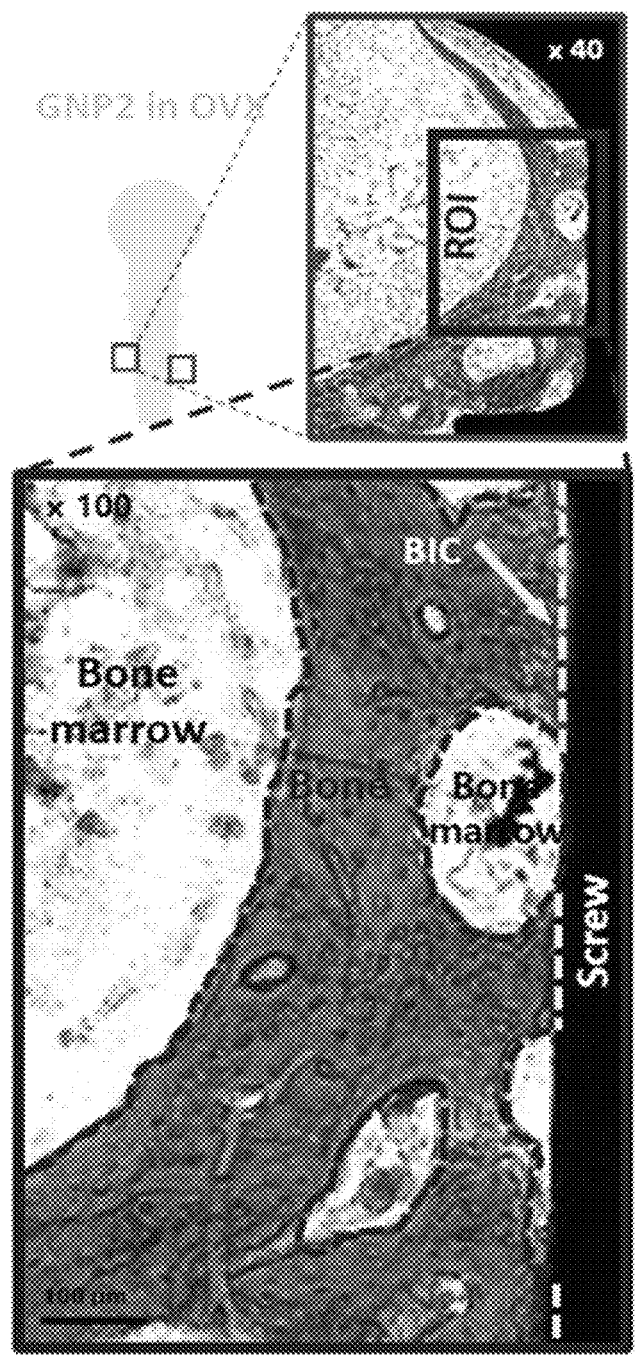
FIG. 14B provides the representative visual images within the ROI after the GNP2 screw insertion into an OVX rabbit model.

FIG. 14B provides the representative 2D images in a GNP2 screw group after Masson-Goldner trichrome staining in an OVX model.

Figure 14C:
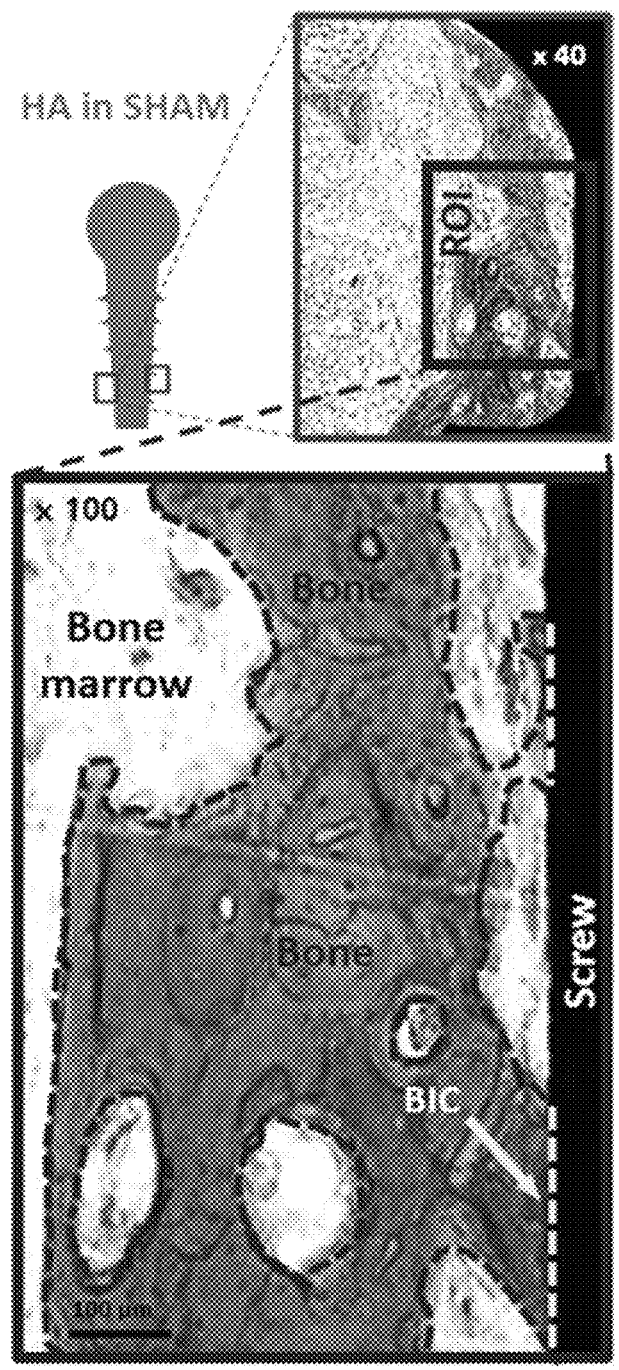
FIG. 14C provides the visual images within the ROI after the insertion of HA coated screws into a SHAM rabbit model.

FIG. 14C provides the representative 2D images in a HA screw group after Masson-Goldner trichrome staining in a SHAM model.

Figure 14D:
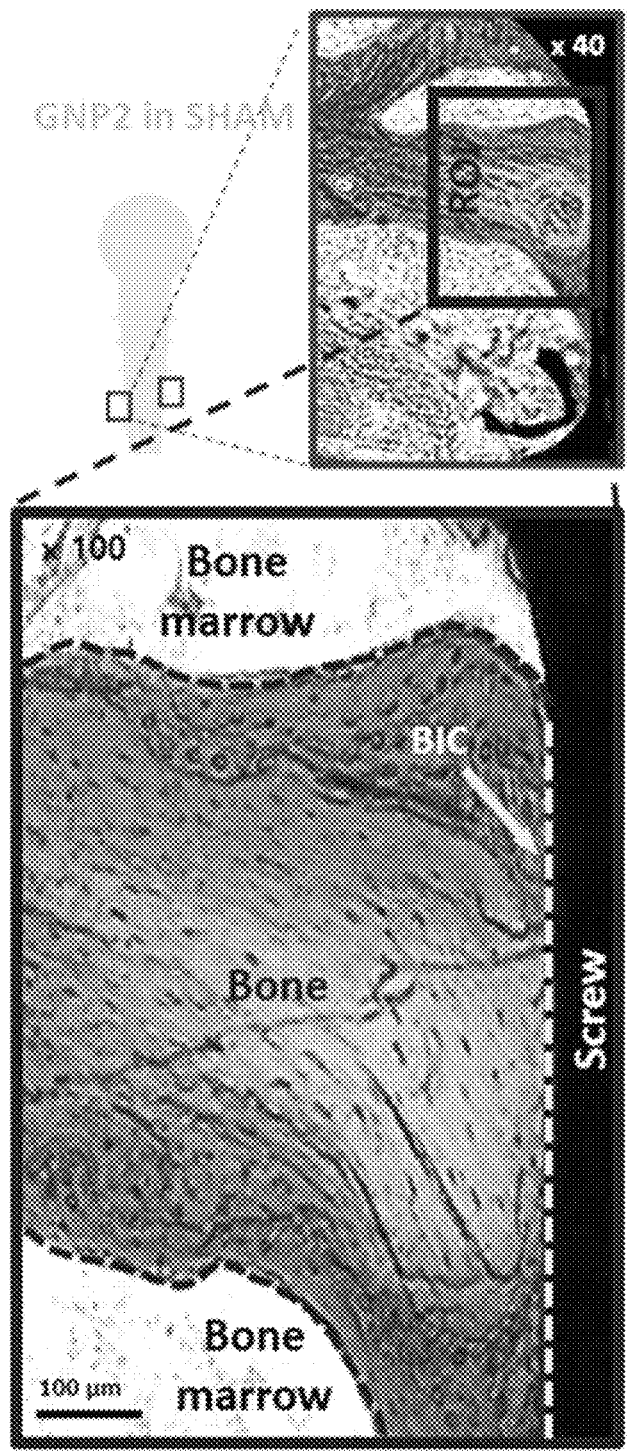
FIG. 14D provides the representative visual images within the ROI after the GNP2 screw insertion into a SHAM rabbit model.

FIG. 14D provides the representative 2D images in a GNP2 screw group after Masson-Goldner trichrome staining in a SHAM model.

The 400×800 µm$^2$ area of the ROI was set as 100% and the bone area stained with green was calculated using the ImageJ software (http://rsb.info.nih.gov/ij/index.html, ImageJ; National Institutes of Health (NIH), Bethesda, MD, USA). The BIC in the ROI were quantified as follows (n=6 per group): The 800 µm length of the entire long axis of screw within the ROI was set as 100%. The bone line in contact with the screw surfaces was calculated. The percentages of BIC were provided in Table 5.

TABLE 5

| BIC (%) | OVX model | | SHAM model | |
|---|---|---|---|---|
| | HA screw | GNP2 screw | HA screw | GNP2 screw |
| N = 1 | 20.3 | 61.0 | 48.3 | 78.0 |
| N = 2 | 25.4 | 57.4 | 55.6 | 68.9 |
| N = 3 | 32.8 | 53.8 | 60.4 | 80.7 |
| N = 4 | 35.9 | 48.8 | 50.7 | 59.7 |
| N = 5 | 40.8 | 50.9 | 58.9 | 70.5 |
| N = 6 | 45.8 | 54.7 | 64.1 | 60.3 |
| Average | 33.5 | 54.4 | 56.3 | 69.7 |
| STDEV | 9.5 | 4.4 | 6.0 | 8.7 |

The BV in the ROI were also quantified as follows (n=6 per group): The 400×800 µm$^2$ area of the ROI was set as 100%. The BV area stained with green was calculated using the ImageJ software. Table 6 provides the measured percentages.

TABLE 6

| BV (%) | OVX model | | SHAM model | |
|---|---|---|---|---|
| | HA screw | GNP2 screw | HA screw | GNP2 screw |
| N = 1 | 44.7 | 55.5 | 74.0 | 80.3 |
| N = 2 | 50.9 | 58.8 | 69.8 | 81.4 |
| N = 3 | 48.5 | 55.9 | 64.9 | 78.9 |
| N = 4 | 55.7 | 61.5 | 70.5 | 85.0 |
| N = 5 | 55.1 | 65.8 | 67.4 | 77.1 |
| N = 6 | 57.3 | 58.1 | 70.1 | 83.9 |
| Average | 52.0 | 59.3 | 69.5 | 81.1 |
| STDEV | 4.9 | 3.9 | 3.1 | 3.0 |

Figure 15:
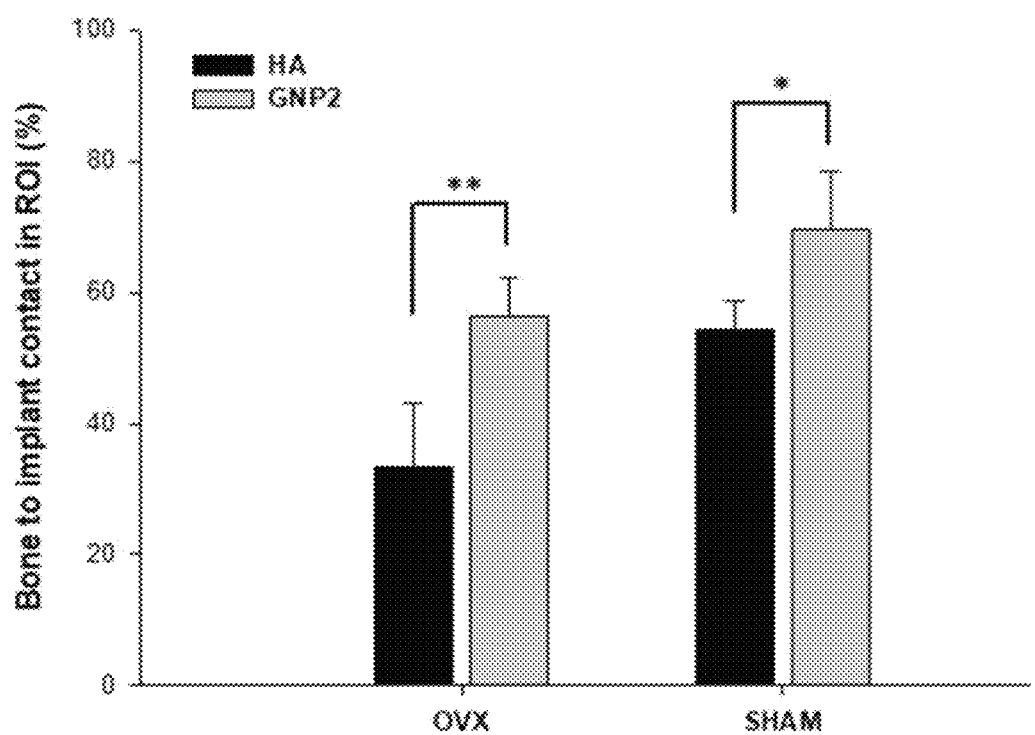
FIG. 15 provides the quantitative percentages (%) of bone to implant contact (BIC)/TV within the designated ROIs after the screw insertion into the OVX or SHAM rabbit models.

FIG. 15 provides the BIC percentages within the ROIs in the OVX and SHAM model (left: HA screw, right: GNP2 screw)

Figure 16:
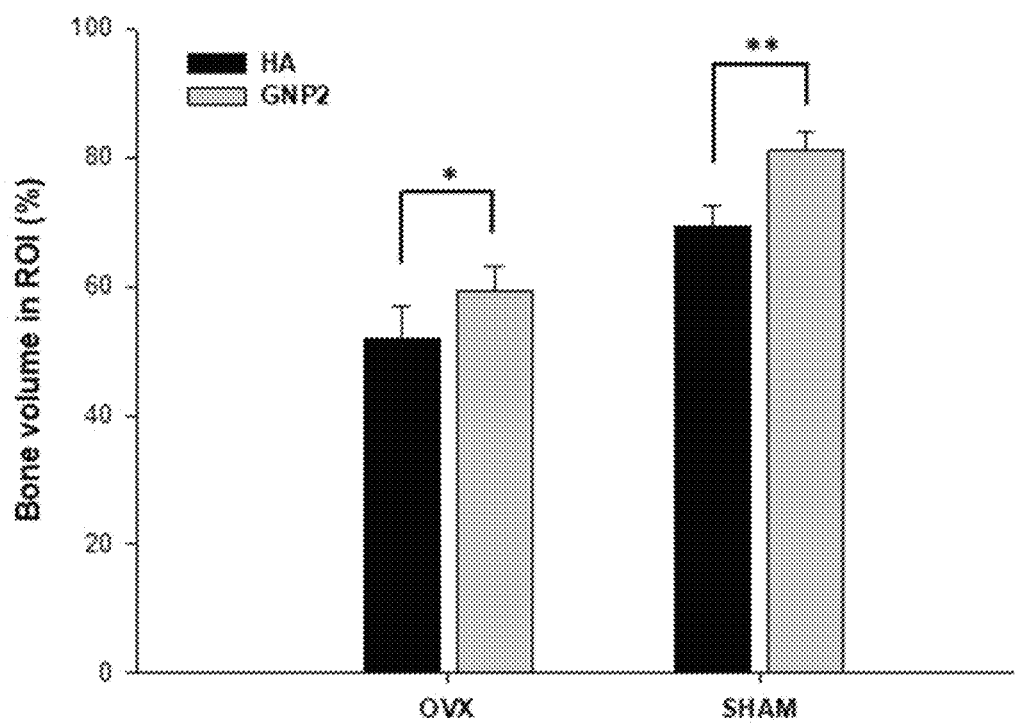
FIG. 16 provides the quantitative percentages of BV within the designated ROIs after the insertion of the HA or GNP2 screws into the OVX or SHAM rabbit models.

FIG. 16 provides the BV percentages within the ROIs in the OVX and SHAM model (left: HA screw, right: GNP2 screw)

As shown in FIGS. 15 and 16, the percentages of BIC and BV in the OVX model were significantly increased in the GNP2 group as compared to the HA group.

This result indicates that double layers of GNPs immobilized screws induced the osteointegration between the inserted area and the implanted screw.

The invention claimed is:

1. A surface-modified medical implant comprising:
   an implant body;
   a first layer of gold nanoparticles; and
   a second layer of gold nanoparticles, wherein the first layer of gold nanoparticles attached to a surface of the implant body via thiol group on the implant body; and wherein the second layer of gold nanoparticles is attached to surface of the first layer of gold nanoparticles via thiol on the surface of the first layer of gold nanoparticle.

2. The surface modified medical implant of claim 1, wherein the implant body comprises titanium, titanium metal or titanium alloy.

3. The surface modified medical implant of claim 1, wherein size of the gold nanoparticles is 10-100 nm.

4. The surface modified medical implant of claim 1, wherein the thiol on the implant body is formed by sequential modification of a $O_2$ membrane on the surface of implant body with alkali and silane.

5. The surface modified medical implant of claim 2, wherein the thiol on the surface of the first layer of gold nanoparticles is formed by sequential modification of the surface of the first layer of gold nanoparticles with alcohol and thiol.

6. The surface modified medical implant of claim 4, wherein the alkali is NaOH and silane is thiolsilane.

7. The surface modified medical implant of claim 5, wherein the alcohol is anhydrous ethanol and thiol is 1,6-hexanedithiol.

8. The surface modified medical implant of claim 1, wherein contact angles between a water drop and the implant surface is 40-45°.

9. The surface modified medical implant of claim 1, wherein the medical implant promotes an osteogenic differentiation before immobilizing gold nanoparticles.

10. The surface modified medical implant of claim 1, wherein the medical implant is a dental or an orthopedic implant.

11. A method of preparing the surface modified medical implant of claim 1 comprising:
   i) oxidizing surface of an implant body;
   ii) treating the oxidized implant surface with alkali to form active OH groups on the surface of the implant body;
   iii) treating the implant body with active OH groups as obtained from step ii) with thiol silane to convert OH to SH groups on the surface of the implant body;
   iv) treating the implant body obtained from step iii) with gold nanoparticles to immobilize a single layer of gold nanoparticles to prepare a medical implant with one layer of gold nanoparticles.

12. The method of claim 11, further comprising:
   v) treating the medical implant with one layer of gold nanoparticles with thiol and alcohol to form active SH groups on the surface of the first layer of gold nanoparticles; and
   vi) treating the medical implant from step v) with gold nanoparticles to immobilize a second layer of gold nanoparticles.

13. The method of claim 11, wherein alkali is NaOH.

14. The method of claim 11, wherein thiol silane is (3-merchaptopropyl) trimethoxysilane.

15. The method of claim 12, wherein the thiol is 1,6-hexanedithiol.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Homo sapiens

<400> SEQUENCE: 1
gagggccaag acgaagacat c                                              21

<210> SEQ ID NO 2
<211> LENGTH: 21
<212> TYPE: DNA
<213> ORGANISM: Homo sapiens

<400> SEQUENCE: 2
cagatcacgt catcgcacaa c                                              21

```
<210> SEQ ID NO 3
<211> LENGTH: 17
<212> TYPE: DNA
<213> ORGANISM: Homo sapiens

<400> SEQUENCE: 3
ccgatgggac cgtggtt                                                  17

<210> SEQ ID NO 4
<211> LENGTH: 21
<212> TYPE: DNA
<213> ORGANISM: Homo sapiens

<400> SEQUENCE: 4
cagcagaggc atttcgtagc t                                             21

<210> SEQ ID NO 5
<211> LENGTH: 21
<212> TYPE: DNA
<213> ORGANISM: Homo sapiens

<400> SEQUENCE: 5
cagttgtccc cacagtagac a                                             21

<210> SEQ ID NO 6
<211> LENGTH: 23
<212> TYPE: DNA
<213> ORGANISM: Homo sapiens

<400> SEQUENCE: 6
gtgatgtcct cgtctgtagc atc                                           23

<210> SEQ ID NO 7
<211> LENGTH: 22
<212> TYPE: DNA
<213> ORGANISM: Homo sapiens

<400> SEQUENCE: 7
cgtaaagacc tctatgccaa ca                                            22

<210> SEQ ID NO 8
<211> LENGTH: 21
<212> TYPE: DNA
<213> ORGANISM: Homo sapiens

<400> SEQUENCE: 8
cggactcatc gtactcctgc t                                             21
```